US010588950B2

(12) United States Patent
Pittman et al.

(10) Patent No.: US 10,588,950 B2
(45) Date of Patent: Mar. 17, 2020

(54) COMPOSITIONS AND METHODS FOR COUNTERACTING FACTOR XA INHIBITION

(71) Applicants: Pfizer Inc., New York, NY (US); The Children's Hospital of Philadelphia, Philadelphia, PA (US)

(72) Inventors: Debra D. Pittman, Windham, NH (US); Rodney M. Camire, Sicklerville, NJ (US); Joachim Fruebis, Bedford, MA (US)

(73) Assignee: PFIZER INC., New York, NY (US)

( * ) Notice: Subject to any disclaimer, the term of this patent is extended or adjusted under 35 U.S.C. 154(b) by 0 days.

(21) Appl. No.: 15/873,416

(22) Filed: Jan. 17, 2018

(65) Prior Publication Data

US 2018/0344819 A1 Dec. 6, 2018

Related U.S. Application Data

(63) Continuation of application No. 14/759,520, filed as application No. PCT/IB2014/058494 on Jan. 23, 2014, now abandoned.

(60) Provisional application No. 61/759,332, filed on Jan. 31, 2013.

(51) Int. Cl.
```
A61K 38/48      (2006.01)
A61K 45/06      (2006.01)
C12N 9/64       (2006.01)
A61K 31/437     (2006.01)
A61K 31/5377    (2006.01)
```

(52) U.S. Cl.
CPC ........ *A61K 38/4846* (2013.01); *A61K 31/437* (2013.01); *A61K 31/5377* (2013.01); *A61K 45/06* (2013.01); *C12N 9/6432* (2013.01); *C12Y 304/21006* (2013.01)

(58) Field of Classification Search
CPC .............. A61K 2300/00; A61K 31/437; A61K 31/5377; A61K 38/4846; A61K 45/06; C12N 9/6432; C12Y 304/21006
See application file for complete search history.

(56) References Cited

U.S. PATENT DOCUMENTS

| | | |
|---|---|---|
| 5,597,799 A | 1/1997 | Wolf |
| 6,133,256 A | 10/2000 | Scarborough et al. |
| 6,262,047 B1 | 7/2001 | Zhu et al. |
| 6,369,080 B2 | 4/2002 | Zhu et al. |
| 6,562,598 B1 | 5/2003 | Himmelspach |
| 6,573,071 B1 | 6/2003 | Himmelspach |
| 6,905,846 B2 | 6/2005 | Himmelspach |
| 6,958,322 B1 | 10/2005 | Himmelspach |
| 7,220,569 B2 | 5/2007 | Himmelspach |
| 7,745,224 B2 * | 6/2010 | Zander ................ G01N 33/96 435/13 |
| 8,153,590 B2 | 4/2012 | Lu et al. |
| 8,268,783 B2 | 9/2012 | Sinha et al. |
| 8,383,386 B2 * | 2/2013 | Camire ................ C12N 9/6432 435/212 |
| 8,436,144 B2 | 5/2013 | Christophe |
| 8,455,439 B2 | 6/2013 | Lu |
| 9,347,051 B2 | 5/2016 | Schulte |
| 9,371,522 B2 | 6/2016 | Camire |
| 9,410,137 B2 | 8/2016 | Camire |
| 9,757,434 B2 * | 9/2017 | Johnson ................ A61K 38/36 |
| 9,896,676 B2 * | 2/2018 | Camire ................ C12N 9/6432 |
| 10,106,786 B2 | 10/2018 | Camire |
| 2003/0138914 A1 | 7/2003 | Himmelspach |
| 2003/0181381 A1 | 9/2003 | Himmelspach |
| 2006/0148038 A1 | 7/2006 | Louvain |
| 2008/0318276 A1 | 12/2008 | Persson et al. |
| 2009/0042787 A1 | 2/2009 | Metzner |
| 2009/0098119 A1 | 4/2009 | Lu |
| 2009/0175931 A1 * | 7/2009 | Camire ................ C12N 9/6432 424/450 |
| 2010/0297257 A1 | 11/2010 | Smith et al. |
| 2011/0015128 A1 | 1/2011 | Sinha et al. |
| 2012/0269788 A1 | 10/2012 | Lu et al. |
| 2014/0050716 A1 | 2/2014 | Polack |
| 2014/0120155 A1 | 5/2014 | Camire |
| 2014/0248259 A1 | 9/2014 | Camire |
| 2015/0182604 A1 | 7/2015 | Johnson et al. |
| 2015/0343033 A1 | 12/2015 | Plantier et al. |
| 2016/0235824 A1 * | 8/2016 | Camire ................ A61K 31/727 |
| 2016/0362673 A1 | 12/2016 | Camire |
| 2016/0375109 A1 * | 12/2016 | Arkin ............. C12Y 304/21006 424/94.64 |
| 2017/0247677 A1 | 8/2017 | Camire |
| 2017/0333535 A1 * | 11/2017 | Johnson ................ A61K 38/36 |

(Continued)

FOREIGN PATENT DOCUMENTS

| | | |
|---|---|---|
| EP | 1820508 | 0/8200 |
| EP | 1539816 | 1/2006 |
| EP | 1728798 | 12/2006 |

(Continued)

OTHER PUBLICATIONS

Weitz. Factor Xa and thrombin as targets for new oral anticoagulants. Thrombosis Research, vol. 127, Supplement 2, pp. S5-S12. (Year: 2011).*
Eerenberg et al. Reversal of Rivaroxaban and Dabigatran by Prothrombin Complex Concentrate. A Randomized, Placebo-Controlled, Crossover Study in Healthy Subjects. Circulation, vol. 124, pp. 1573-1579. (Year: 2011).*
INR calculator. Accessed online at https://www.empr.com/medical-calculators/inr-calculator/article/170184/ on Nov. 16, 2018, 3 pages. (Year: 2018).*
Connolly et al, "Andexanet Alfa for Acute Major Bleeding Associated with Factor Xa Inhibitors" New England Journal of Medicine, vol. 375, No. 12, pp. 1131-1141, 2016.

(Continued)

*Primary Examiner* — Marcela M Cordero Garcia

(57) ABSTRACT

The disclosure provides compositions and methods for counteracting the effects of direct activated Factor X (FXa) inhibitors in a subject by administering a variant of FXa.

20 Claims, 17 Drawing Sheets

Specification includes a Sequence Listing.

(56) References Cited

U.S. PATENT DOCUMENTS

| | | | |
|---|---|---|---|
| 2018/0251745 A1* | 9/2018 | Camire | C12N 9/6432 |
| 2019/0231856 A1* | 8/2019 | Arkin | A61K 38/4846 |

FOREIGN PATENT DOCUMENTS

| | | |
|---|---|---|
| EP | 1948690 | 7/2008 |
| EP | 1991255 | 11/2008 |
| WO | 1998038317 | 9/1998 |
| WO | 1998038318 | 9/1998 |
| WO | 2000015250 | 3/2000 |
| WO | 2001070763 | 9/2001 |
| WO | 2003035861 | 5/2003 |
| WO | 2004005347 | 1/2004 |
| WO | 2007059513 | 5/2007 |
| WO | 2007096116 | 8/2007 |
| WO | 2009042962 | 4/2009 |
| WO | 2011008885 | 1/2011 |
| WO | 2012069139 | 5/2012 |
| WO | 2013049804 | 4/2013 |
| WO | 2013123248 | 8/2013 |
| WO | 2014118677 | 8/2014 |
| WO | 2015044836 | 4/2015 |
| WO | 2015066606 | 5/2015 |
| WO | 2015110939 | 7/2015 |

OTHER PUBLICATIONS

Imberti et al, "Emergency reversal of anticoagulation with vitamin K antagonists with 3-factor prothrombin complex concentrates in patients with major bleeding" J Thromb Thrombolysis, vol. 36, pp. 102-108, 2013.

Mueck et al. "Clinical Pharmacokinetic and Pharmacodynamic Profile of Rivaroxaban" Clin. Pharmacokinet., vol. 53, pp. 1-16, 2014.

Quinlan et al, "Four-Factor Prothrombin Complex Concentrate for Urgent Reversal of Vitamin K Antagonists in Patients With Major Bleeding" Circulation, vol. 128, pp. 1179-1181, 2013.

Sawka et al, "Erythrocyte, plasma, and blood volume of healthy young men" Medicine and Science. in Sports and Exercise, vol. 24, No. 4, pp. 447-453, 1992.

Rezaie, A. R., Neuenschwander, P.F., Morrissey, J.H., and Esmon, C.T. (1993) Analysis of the functions of the first epidermal growth factor-like domain of factor X. J. Biol. Chem. 268, 8176-8180.

Robison, D., Furie, B., Furie, B. C., and Bing, D. H. (1980) Active site of bovine factor X. Characterization using substituted benzamidines as competitive inhibitors and affinity-labeling reagents. J.Biol. Chem. 255, 2014-2021.

Rudinger, J. "Characteristics of the amino acids as components of a peptide hormone sequence." In Peptide Hormones (JA Parsons, ed.) University Park Press.1976:1-7.

Rudolph, A.E., et al., "Expression, purification, and characterization of recombinant human factor X." Protein Expr Purif., 1997 Aug;10(3):373-8.

Schlachterman, A et al., Factor V Leiden improves in vivo hemostasis in murine hemophilia models, J Thromb Haemost 3(12)2730-2737 (Dec. 2005).

Stanley, T. B., Humphries, J., High, K. A., and Stafford, D. W. (1999) Amino acids responsible for the reduced affinities of vitamin K-dependent propeptides for the carboxylase. Biochemistry 38, 15681-15687.

Stanley, T. B., Jin, D. Y., Lin, P., and Stafford, D. W. (1999) The propeptides of the vitamin K-dependent proteins possess different affinities for the vitamin K dependent carboxylase. J. Biol. Chem. 274, 16940-16944.

Strandberg, L, et al. "Variants of tissue-type plasminogen activator with substantially enhanced response and selectivity toward fibrin co-factors." J Biol Chem. Oct. 6, 1995; 270(40)23444-9.

Sun, T., et al. "Vitamin K epoxide reductase significantly improves carboxylation in a cell line overexpressing factor X." Blood, 106(12):3811-3815 (2005).

Sziegoleit, A., A human pancreatic chymotrypsin: biochemical and molecular characterization, GenBank accession No. CAA74031.1, direct submission Jun. 10, 1997.

Tachias, K. And Madison, E. (1996) Converting tissue-type plasminogen activator into a zymogen. J.Biol.Chem. 271, 28749-28752.

Tachias, K. And Madison, E. (1997) Converting tissue type plasminogen activator into a zymogen. Important role of Lys156. J.Biol.Chem. 272, 28-31.

Thalji N., Patel-Hett S., Fruebis J., Pittman D., Camire R.M. Reversal of direct factor Xa inhibitors using factor Xa zymogen-like variants. Journal of Thrombosis and Haemostasis. 11 (pp. 167), Jul. 2013. Abstract from 24th Congress of the International Society on Thrombosis and Haemostasis.

Toso, R., et al. "Factor VII mutant V154G models a zymogen-like form of factor VIIa." The Biochemical Journal, 369 (3):563-571 (Feb. 1, 2003).

Toso, R., et al. "Factor VII variants as tools to study Factor VIIa salt bridge formation." Database Biosis. Biosciences, Information Service, Philadelphia, PA & Blood, 98(11):526a (Nov. 16, 2001) [Abstract].

Toso, R.. et al. "The conformational switch from the factor X zymogen to protease state mediates exosite expression and prothrombinase assembly." Journal of Biological Chemistry, 283(27):18627-18635 (Jul. 2008).

Venkateswarlu, D., Perera, L., Darden, T., and Pedersen, L.G. (2002) Structure and dynamics of zymogen human blood coagulation factor X. Biophys. J. 82, 1190-1206.

Wells, Ja "Additivity of mutational effects in proteins." Biochemistry. Sep. 18, 1990;29(37):8509-17.

Wolf, D.L, et al. "Design of Constructs for the Expression of Biologically Active Recombinant Human Factors X and Xa." J Biol Chem. Jul. 25, 1991;266(21):13726-13730.

Zhong, D. Bajaj, M. S. Sclunidt, A. E., and Bajaj, S. P. (2002) "The N-terminal EGF-like domain in factor IX and factor X represents an important recognition motif for binding to tissue factor." J.Biol. Chem. 277, 3622-3631.

International Preliminary Report on Patentability (IPRP) PCT/US2006/060927 (WO 2007/059513).

Written Opinion of the International Search Authority PCT/US2006/060927 (WO 2007/059513).

International Search Report (ISR) PCT/US2006/060927 (WO 20071059513).

European Search Report EP1948690 A1 (EP06846312.4).

Supplementary European Search Report EP1948690 A1 (EP06846312.4).

International Preliminary Report on Patentability (IPRP) PCT/US2012/058279 (WO 2013/049804).

International Search Report (ISR) PCT/US2012/058279 (WO 20131049804).

Written Opinion of the International Search Authority PCT/US2012/058279 (WO 2013/049804).

International Preliminary Report on Patentability (IPRP) PCT/IB2014/058494 (WO 2014/118677).

Written Opinion of the International Search Authority PCT/IB2014/058494 (WO 2014/118677).

International Search Report (ISR) PCT/IB2014/058494 (WO 2014/118677).

International Preliminary Report on Patentability (IPRP) PCT/US2014/063676 (WO 2015/066606).

Written Opinion of the International Search Authority PCT/US2014/063676 (WO 2015/066606).

International Search Report (ISR) PCT/US2014/063676 (WO 2015/066606).

Greene L.A., Thalji N. K., Raffini L.J., Camire R.M., Zymogen-like FXA variant as a short-acting warfarin reversal agent: Pre-clinical evaluation and mechanism of action. Blood 124(21), Dec. 6, 2014. Abstract from 2014 Annual Meeting of the American Society of Hematology.

Greene L.A., Thalji N. K., Camire R.M., Zymogen-like FXA variant as novel warfarin reversal strategy: Pre-clinical evaluation and mechanism of action. Journal of Thrombosis and Haemostasis 13 (p. 491), Jun. 2015. Abstract from the 25th Congress of the International Society on Thrombosis and Haemostasis.

(56) References Cited

OTHER PUBLICATIONS

Lu, G et al., Reconstructed recombinant factor Xa as an antidote to reverse anticoagulation by factor Xa inhibitors, J Thromb Haemos, vol. 7, suppl. 2, p. 309 (Abstract OC-TH-107), Jul. 1, 2009.
Reema J., Patel-Nett S., Camire R.M., Fruebis J., Pittman D., A zymogen-like factor xa improves hemostasis in a murine bleeding model. Blood 124(21), Dec. 6, 2014. Abstract from 2014 Annual Meeting of the American Society of Hematology.
Thalji N. K., Ivanciu L, Jasuja R., Patel-Nett S., Fruebis J., Pittman D., Camire R.M., Zymogen-like FXa is a potent bypassing agent for reversal of direct FXa inhibitors in vivo. Blood 124(21), Dec. 6, 2014. Abstract from 2014 Annual Meeting of the American Society of Hematology.
Thalji N. K., Patel-Hett S., Jasuja R., Fruebis J., Pittman D., Camire R.M. Zymogen-like FXa is an effective pro-hemostatic to reverse the anticoagulant effects of direct FXa inhibitors. Blood. 122(21). Nov. 15, 2013. Abstract from 2013 Annual Meeting of the American Society of Hematology.
Asmis, LM et al., Rivaroxaban: Quantification by anti-FXa assay and influence on coagulation tests, A study in 9 Swiss aboratories. Thromb Res., 129:492-498 (2012).
Barrett, YC et al., Clinical laboratory measurement of direct factor Xa inhibitors: Anti-Xa assay is preferable to prothrombin time assay. Thromb Haemost. 104:1263-71 (2010), published online Oct. 26, 2010.
Graff, et al., Monitoring effects of direct FXa-inhibitors with a new one-step prothrombinase-induced clotting time (PiCT) assay: comparative in vitro investigation with heparin, enoxaparin, fondaparinux and Dx 9065a, Int J Clin Pharmacol Ther., 45(4):237-43 (2007).
Harder, S et al., Monitoring direct FXa-inhibitors and fondaparinux by Prothrombinase-induced Clotting Time (PiCT): relation to FXa-activity and influence of assay modifications, Thromb Res., 123:396-403 (2008), published online Jun. 24, 2008.
Lu, G, et al., A specific antidote for reversal of anticoagulation by direct and indirect inhibitors of coagulation factor Xa, Nature Medicine 19(4):446-451 (2013), published online Mar. 3, 2013; and 3 pages Supplemental figures.
Perzborn, E et al., the discovery and development of rivaroxaban, an oral, direct factor Xa inhibitor. Nat Rev Drug Discov. Jan 2011; 10:61-75.
Pinto, DJP et al., The emergence of factor Xa inhibitors for the treatment of cardiovascular diseases: a patent review. Expert Opin. Ther. Patents 22(6):645-661 (2012).
Pinto, DJP et al., Discovery of 1-(4-Methoxyphenyl)-7-oxo-6-(4-(2-oxopiperidin-1-yl)phenyl)-4,5,6,7-tetrahydro-1H-byrazolo[3,4-c]pyridine-3-carboxamide (Apixaban, BMS-562247), a Highly Potent, Selective, Efficacious, and Orally Bioavailable Inhibitor of Blood Coagulation Factor Xa. J. Med. Chem. 50:5339-5356 (2007), published online Oct. 3, 2007.
"SEQ ID No. 2 mi file" uploaded as partial result from PTO search file entitled "Sequence Search-20070801_095501_pct-us06-60-20070801_095501_pct-us06-60927-2-.mi" in order to demonstrate homology of claimed sequence to previously published sequence (2007); (cited in International Search Report of PCT/US2006/60927).
Ai-Tamimi et al., Coagulation-induced shedding of platelet glycoprotein VI mediated by factor Xa. Blood 117:3912-3920 (Sep. 18, 2011).
Bajaj and Birktoft, "Human Factor IX and Factor IXa", Methods Enzymol.; 222; pp. 96-128; 1993;.
Bianchini, E.P., et al. "Mapping of the catalytic groove preferences of factor Xa reveals an inadequate selectivity for its macromolecule substrates." J Biol Chem. Jun. 7, 2002;277(23):20527-34. Epub Mar. 29, 2002.
Bock et al. "Isolation of human blood coagulation α-factor Xa by soybean-trypsin inhibitor-Sepharose chromatography and its active-site titration with fluorescein mono-p-guanidinobenzoate." Arch. Bloch. Biophys. 273; pp. 375-388; 1989.

Bode et al. "The refined 1.9 Å crystal structure of human alpha-thrombin: interaction with D-Phe-Pro-Arg chloromethylketone and significance of the Tyr-Pro-Trp insertion segment." Embo J.; 8(11); pp. 3467-3475; 1989.
Brandstetter et al., "X-ray Structure of Active Site-inhibited Clotting Factor Xa."; J. Biol. Chem.; 271; pp. 29988-29992 1996.
Bunce, M. et al., "Zymogen-like factor Xa variants restore thrombin generation and effectively bypass the intrinsic pathway in vitro." Blood, Jan. 6, 2011; vol. 117, No. 1:290-298.
Bunce, Matthew W.; Toso, Raffaella; Arruda, Valder R.; Camire, Rodney M. Zymogen-Like Factor Xa Variants Restore Thrombin Generation and Effectively Bypass the Intrinsic Pathway in Vitro. Blood. 112(11). Nov. 16, 2008. Abstract from 2008 Annual Meeting of the American Society of Hematology.
Camire R.M., Bunce M., Ivanciu L., Toso R., Downey H., Liu J., Arruda V. Novel factor XA variants for improving hemostasis in hemophilia. Journal of Thrombosis and Haemostasis. 7 (S2) (pp. 96), Jul. 2009. Abstract from 22nd Congress of the International Society of Thrombosis and Haemostasis.
Camire R.M., Bunce M., Ivanciu L., Toso R., Downey H.D., Liu J.-H., Arruda V.R. The development of novel hemostatic bypassing molecules. Blood. 114(22). Nov. 20, 2009. Abstract from 2009 Annual Meeting of the American Society of Hematology.
Camire, R. M., Larson, P. J., Stafford, D. W, and High, K. A. (2000) Enhanced γ-carboxylation of recombinant factor X using a chimeric construct containing the prothrombin propeptide. Biochemistry 39, 14322-14329.
Camire, R. "Prothrombinase assembly and S1 site occupation restore the catalytic activity of FXa impaired by mutation at the sodium-binding site." Journal of Biological Chemistry, 277(40):37863-37870 (Oct. 4, 2002).
Chase, T. And Shaw, E. (1969) Comparison of the esterase activities of trypsin, plasmin, and thrombin on guanidinobenzoate esters. Titration of the enzymes. Biochemistry. 8, 2212-2224.
Dahlback, B. And Stenflo, J. (1978) Binding of bovine coagulation factor Xa to platelets. Biochemistry 17, 4938-4945.
Duckert, P., et al., Prediction of proprotein convertase cleavage sites, Protein Engineering, Design & Selection 17 (1):107-112 (2004).
Eigenbrot, C., Kirchhofer, D., Dennis, M. S., Santell, L., Lazarus, R. A., Stamos, J., and Ultsch MH; "The factor VII zymogen structure reveals reregistration of beta strands during activation." Structure 9, 627-636; 2001.
Friedrich, R., et al. "Staphylocoagulase is a prototype for the mechanism of cofactor-induced zymogen activation." Nature, 425: 535-539 (Oct. 2, 2003).
Furie, B. And Furie, B. C. (1976) Spectral changes in bovine factor X associated with activation by the venom coagulant protein Vipera russelli. J.Biol. Chem. 251, 6807-6814.
Guo, H.H., et al. "Protein tolerance to random amino acid change." Proc. Natl. Acad. Sci. USA.;101 (25):9205-10; Jun. 22, 2004.
Hedstrom, L., et al. "Hydrophobic interactions control zymogen activation in the trypsin family of serine proteases." Biochemistry, 35(14): 4515-4523 (1996).
Hertzberg, M, "Biochemistry of Factor X", Blood Reviews 8:56-62 (1994).
Holt, K., Human Coagulation Factor X, Swiss Prot accession no. Q5JVE7, direct submission May, 2005.
Hult, K, et al. "Engineered enzymes for improved organic synthesis." Curr Opin Biotechnol. Aug. 2003;14(4):395-400.
Ivanciu L., et al., "A zymogen-like factor Xa variant corrects the coagulation defect in hemophilia." Nat. Biotechnol. 29:1028-33 (2011); and 11 pages supplemental figures and tables.
Ivanciu L., Camire R.M. "Modulation of FXa zymogenicity yields variants that improve hemostasis in hemophilia." Journal of Thrombosis and Haemostasis. 11 (pp. 270), Jul. 2013. Abstract from 24th Congress of the International Society of Thrombosis and Haemostasis.
Ivanciu L, Camire R.M. "Selective alteration of FXa zymogenicity provides a dynamic range of variants that improve hemostasis in hemophilia." Blood. 118(21). Nov. 18, 2011. Abstract from 2011 Annual Meeting of the American Society of Hematology.
Ivanciu L., Toso R., Schlachterman A., Downey H., Liu J., Arruda V.R., Camire R.M. Zymogen-like factor Xa variants improve hemostasis

(56) References Cited

OTHER PUBLICATIONS in hemophilia mice. Journal of Thrombosis and Haemostasis. 7 (S2) (pp. 82-83), Jul. 2009. Abstract from 22nd Congress of the International Society of Thrombosis and Haemostasis.
Ivanciu, Lacramioara; Toso, Raffaella; Schlachterman, Alexander; Downey, Harre; Liu, Jain-Hua; Arruda, Valder R.; Camire, Rodney M.; "Factor Xa Variants as Novel Bypass Agents for the Treatment of Hemophilia in Murine Models." Blood. 112(11). Nov. 16, 2008. Abstract from 2008 Annual Meeting of the American Society of Hematology.
Jesty et al., "The activation of coagulation factor X", J Biot Chem. Jun. 25, 1975;250(12):4497-504.
Kamal, Ah, et al., "How to interpret and pursue an abnormal prothrombin time, activated partial thromboplastin time, and bleeding time in adults", Mayo Clin Proc. 82(7):864-873 (2007).
Keyt, B., Furie, B. C., and Furie, B. (1982) "Structural transitions in bovine factor X associated with metal binding and zymogen activation. Studies using conformational-specific antibodies." J. Biol. Chem. 257, 8687-8695.
Khan, A.R., et al. "Molecular mechanisms for the conversion of zymogens to active proteolytic enzymes." Protein Science. 1998;7(4):815-836.
Larson, P. J., Camire, R. M., Wong, D., Fasano, N. C., Monroe, D. M., Tracy, P. B., and High, K. A. (1998) "Structure/function analyses of recombinant variants of human factor Xa: Factor Xa incorporation into prothrombinase on the activated platelet surface is not mimicked by synthetic phospholipid vesicles." Biochemistry 37, 5029-5038.
Madison, E., Kobe, A., Gething, M., Sambrook, J. F., and Goldsmith, E. (1993) "Converting tissue plasminogen activator to a zymogen: A regulatory triad of Asp-His-Ser." Science 262, 419-421.
Madoiwa, S. et al., "Autoantibody against prothrombin aberrantly alters the proenzyme to facilitate formation of a complex with its physiological inhibitor antithrombin III without thrombin conversion," Blood 97(12):3783-3789 (2001).
Maekawa H. et al., Molecular defect in factor IX Tokyo: substitution of valine-182 by alanine at position P2' in the second cleavage site by factor XIa resulting in impaired activation. Biochemistry, 32, 6146-6151 (1993).
Miletich, J.P., Jackson, C. M., and Majerus, P. W. (1978) "Properties of the factor Xa binding site on human platelets." J.Biol.Chem. 253, 6908-6916.
Ngo, J.T., et al. "Computational Complexity, Protein Structure Prediction and the Levinthal Paradox." In The Protein Folding Problem and Tertiary Structure Prediction, K.M. Merz and S.M. Le Grand, eds., Birkhäuser Boston (1994), pp. 192-495.
Persson, E., Hogg, P. J., and Stenflo, J. (1993) Effects of Ca2+ binding on the protease module of factor Xa and its interaction with factor Va: evidence for two Gla-independent Ca2+ binding sites in factor Xa. J Biol Chem 268, 22531-22539.
Persson, E., Valcarce, C., and Stenflo, J. (1991) The γ-carboxyglutamic acid and epidermal growth factor-like domains of factor X. Effect of isolated domains on prothrombin activation and endothelial cell binding of factor X. J Biol Chem 266, 2458.
Pittman D., Nichols T., Camire R., Toso R., Merricks E., Raymer R., De Friess N., Leary B., Pamg C., Arkin S., Fruebis J. A factor Xa variant restores hemostasis in a hemophilia a dog model. Haemophilia. 18 (pp. 87-88), Jul. 2012. Absract from 30th International Congress of the World Federation of Hemophilia.
Pittman D., Shields K., Rose-Miranda R., Losey H., Erbe D., Ivanciu L. A novel factor Xa variant for treatment of bleeding disorders. Haemophilia. 16 (pp. 44-45), Jul. 2010. Abstract from 29th International Congress of the World Federation of Hemophilia.
Raju, TS, et al., Species-specific variation in glycosylation of IgG: evidence for the species-specific sialylation and branch-specific galactosylation and importance for engineering recombinant glycoprotein therapeutics, Glycobiology 10 (5):477-486 (2000).
Renatus, M., Engh, R A., Stubbs, M. T., Huber, R., Fischer, S., Kohnert, U., and Bode, W. (1997) Lysine 156 promotes the anomalous proenzyme activity of tPA: X-ray crystal structure of single-chain human tPA. EMBO J 16, 4797-4805.
Rezaie, A. R (2000) Identification of basic residues in the heparin-binding exosite of factor Xa critical for heparin and factor Va binding. J. Biol. Chem. 275, 3320-3327.
Rezaie, A. R. (1996) Role of residue 99 at the S2 subsite of factor Xa and activated protein C in enzyme specificity. J. Biol. Chem. 271, 23807-23814.
Rezaie, A. R. and Esmon, C. T. (1994) Asp-70 to Lys mutant of factor X lacks high affinity Ca2+ binding site yet retains function. J. Biol. Chem. 269, 21495-21499.
Rezaie, A. R. And Esmon, C. T. (1995) Contribution of residue 192 in factor Xa to enzyme specificity and function. J. Biol. Chem. 270, 16176-16181.
Rezaie, A. R. and He, X. (2000) Sodium binding site of factor Xa: Role of sodium in the prothrombinase complex. Biochemistry 39, 1817-1825.
Slide presentation, entitled "Reversal of Factor Xa Inhibitors Using Factor Xa Zymogen-Like Variants," including certain results relating to rivaroxaban on slide 16, used by Nabil Thalji, an Md PhD student then in the laboratory of Dr. Rodney Camire, during a brief (less than 10 minute) talk before students and faculty of the University of Pennsylvania School of Medicine at a Medical Scientist Training Program (MSTP) Retreat held at Villanova University on Aug. 1, 2012.
Agenda of the MSTP Retreat held at Villanova University on Aug. 1, 2012 during which Nabil Thalji presented the slides in NPL Document #1 (above). Believed to correspond to document D3 in the ISR in PCT/IB2014/058494.
Restriction requirement in U.S. Appl. No. 15/031,077 (dated Sep. 26, 2017).
Amendment and response to restriction requirement in U.S. Appl. No. 15/031,077 (dated Jan. 26, 2018).
Non-Final Office action in U.S. Appl. No. 15/031,077 (dated Apr. 20, 2018).
Amendment and Response to Non-Final Office Action in U.S. Appl. No. 15/031,077 (dated Oct. 22, 2018).
Final Office Action in U.S. Appl. No. 15/031,077 (dated Jan. 11, 2019).
Request for Continued Prosecution and Amendment and Response to Final Office Action in U.S. Appl. No. 15/031,077 (dated Jul. 11, 2019).
Toso, Raffaella; Zhu, Hua; Camire, Rodney M., Alteration of the factor X zymogen to protease transition provides evidence for allosteric linkage between the S1 and FVa binding sites. Blood. 106(11, Part 1). Nov. 16, 2005. Abstract from 2005 Annual Meeting of the American Society of Hematology.
Thalji N.K., Patel-Hett S., Jasuja R., Fruebis J., Pittman D., Camire R.M., Zymogen-like FXa is an effective pro-hemostatic to reverse the anticoagulant effects of direct FXa inhibitors. Blood 122(21), Oct. 21, 2013. Abstract from 2013 Annual Meeting of the American Society of Hematology.
Shah, N., Rattu, M.A., Reversal Agents for Anticoagulants: Focus on Andexanet Alfa, Am. Med. Student Res. J., 1:16-28 (2014).
Lu, G. et al., "Recombinant antidote for reversal of anticoagulation by factor Xa inhibitors", Blood, vol. 112:983, Nov. 16, 2008.
Bode, W, et al. "The refined 1.9-A X-ray crystal structure of D-Phe-Pro-Arg chloromethylketone-inhibited human alpha-thrombin: structure analysis, overall structure, electrostatic properties, detailed active-site geometry, and structure-function relationships." Protein Sci. 1992 Apr;1(4):426-71.
Thalji, N. K., "Reversal of Direct Factor Xa Inhibitors Using Factor Xa Zymogen-Like Variants." Text of a research abstract submitted to the 28th Annual National MD/PhD Student Conference held in Keystone, Colorado Jul. 26th-28th, 2013.
Quade-Lyssy et al., "Engineered Factor VII, Factor Ix, and Factor X Variants for Hemophilia Gene Therapy" J. Genetic Syndromes Gene Therapy, (2012), S1:013; 1-7.
Turpie, AGG, Oral, Direct Factor Xa Inhibitors in Development for the Prevention and Treatment of Thromboembolic Diseases. Arterioscler Thromb Vasc Biol. Jun. 2007; 27:1238-47, published online Mar. 22, 2007.

(56) References Cited

OTHER PUBLICATIONS

Hollenbach, S et al., Bolus administration of PRT064445, a recombinant Factor Xa inhibitor antidote, reverses blood loss and PD markers in a rat model following enoxaparin induced anticoagulation, European Heart Journal, vol. 33, No. Suppl, Jan. 1, 2012, pp. 309-310.

* cited by examiner

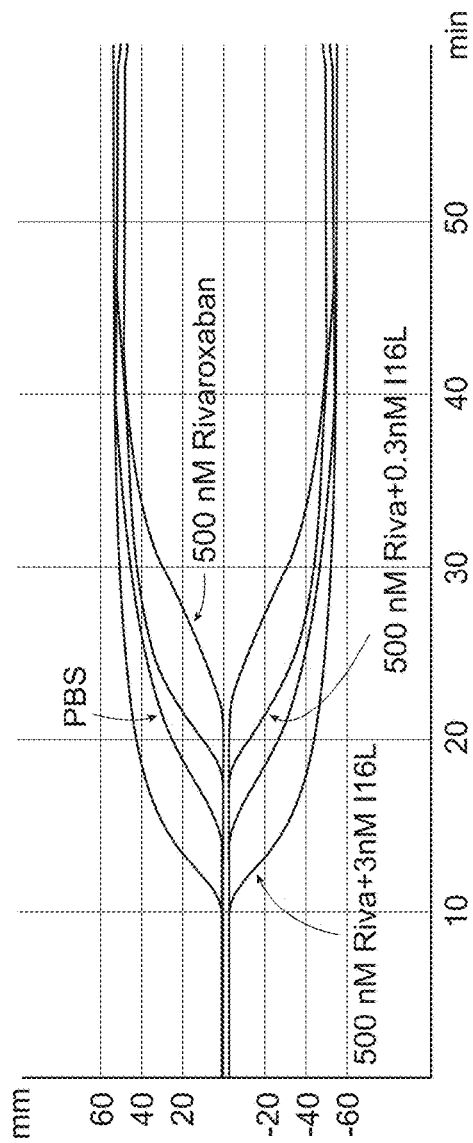
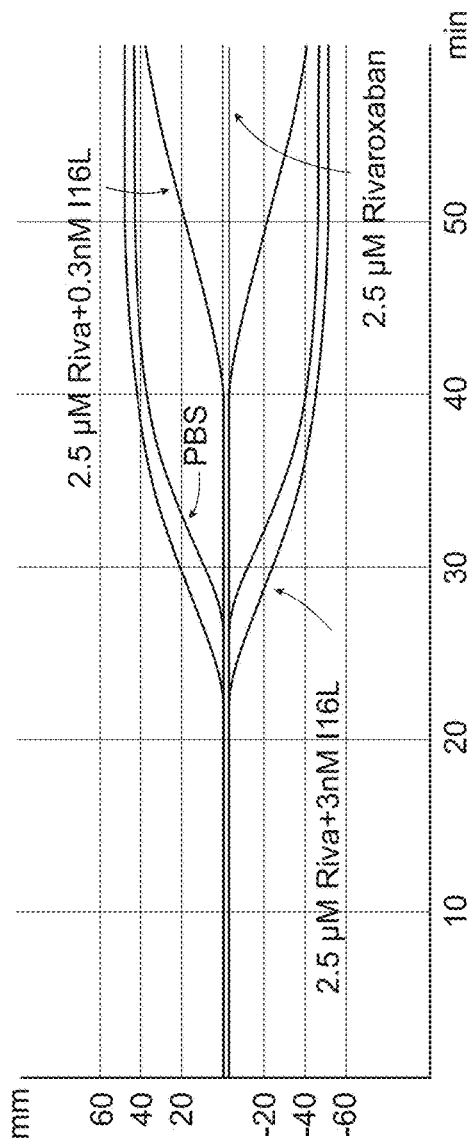
FIG. 8A
FIG. 8B

FIG. 14

Human Factor X Preprotein (SEQ ID NO:1)

```
  1  MGRPLHLVLL  SASLAGLLLL  GESLFIRREQ  ANNILARVTR  ANSFLEEMKK  GHLERECMEE
 61  TCSYEEAREV  FEDSDKTNEF  WNKYKDGDQC  ETSPCQNQGK  CKDGLGEYTC  TCLEGFEGKN
121  CELFTRKLCS  LDNGDCDQFC  HEEQNSVVCS  CARGYTLADN  GKACIPTGPY  PCGKQTLERR
181  KRSVAQATSS  SGEAPDSITW  KPYDAADLDP  TENPFDLLDF  NQTQPERGDN  NLTRIVGGQE
241  CKDGECPWQA  LLINEENEGF  CGGTILSEFY  ILTAAHCLYQ  AKRFKVRVGD  RNTEQEEGGE
301  AVHEVEVVIK  HNRFTKETYD  FDIAVLRLKT  PITFRMNVAP  ACLPERDWAE  STLMTQKTGI
361  VSGFGRTHEK  GRQSTRLKML  EVPYVDRNSC  KLSSSFIITQ  NMFCAGYDTK  QEDACQGDSG
421  GPHVTRFKDT  YFVTGIVSWG  EGCARKGKYG  IYTKVTAFLK  WIDRSMKTRG  LPKAKSHAPE
481  VITSSPLK
```

FIG. 15

Human Factor X Preprotein cDNA (SEQ ID NO:2)

```
  1  GACTTTGCTC CAGCAGCCTG TCCCAGTGAG GACAGGGACA CAGTACTCGG CCACACCATG
 61  GGGCGCCCAC TGCACCTCGT CCTGCTCAGT GCCTCCCTGG CTGGCCTCCT GCTGCTCGGG
121  GAAAGTCTGT TCATCCGCAG GGAGCAGGCC AACAACATCC TGGCGAGGGT CACGAGGGCC
181  AATTCCTTTC TTGAAGAGAT GAAGAAAGGA CACCTCGAAA GAGAGTGCAT GGAAGAGACC
241  TGCTCATACG AAGAGGCCCG CGAGGTCTTT GAGGACAGCG ACAAGACGAA TGAATTCTGG
301  AATAAATACA AAGATGGCGA CCAGTGTGAG ACCAGTCCTT GCCAGAACCA GGGCAAATGT
361  AAAGACGGCC TCGGGGAATA CACCTGCACC TGTTTAGAAG GATTCGAAGG CAAAAACTGT
421  GAATTATTCA CACGGAAGCT CTGCAGCCTG GACAACGGGG ACTGTGACCA GTTCTGCCAC
481  GAGGAACAGA ACTCTGTGGT GTGCTCCTGC GCCCGCGGGT ACACCCTGGC TGACAACGGC
541  AAGGCCTGCA TTCCCACAGG GCCCTACCCC TGTGGGAAAC AGACCCTGGA ACGCAGGAAG
601  AGGTCAGTGG CCCAGGCCAC CAGCAGCAGC GGGGAGGCCC GAGAACCCCT CACATGGAAG
661  CCATATGATG CAGCCGACCT GGACCCCACC TCGACCTGCT TCGACTTCAAC CCAGGAATGC
721  CAGACGCAGC CTGAGAGGGG CGACAACAAC CTCACCAGGA TCGTGGGAGG CCAGGAATGC
781  AAGGACGGGG AGTGTCCCTG GCAGGCCCTG CTCATCAATG AGGAAAACGA GGGTTTCTGT
```

FIG. 15 continued

```
 841  GGTGGAACCA  TTCTGAGCGA  GTTCTACATC  CTAACGGCAG  CCCACTGTCT  CTACCAAGCC
 901  AAGAGATTCA  AGGTGAGGGT  AGGGGACCGG  AACACGGAGC  AGGAGGAGGG  CGGTGAGGCG
 961  GTGCACGAGG  TGGAGGTGGT  CATCAAGCAC  AACCGGTTCA  CAAAGGAGAC  CTATGACTTC
1021  GACATCGCCG  TGCTCCGGCT  CAAGACCCCC  ATCACCTTCC  GCATGAACGT  GGCGCCTGCC
1081  TGCCTCCCCG  AGCGTGACTG  GGCCGAGTCC  ACGCTGATGA  CGCAGAAGAC  GGGGATTGTG
1141  AGCGGCTTCG  GGCGCACCCA  CGAGAAGGGC  CGGCAGTCCA  CCAGGCTCAA  GATGCTGGAG
1201  GTGCCCTACG  TGGACCGGCAA  CAGCTGCAAG  CTGTCCAGCA  GCTTCATCAT  CACCCAGAAC
1261  ATGTTCTGTG  CCGGCTACGA  CACCAAGCAG  GAGGATGCCT  GCCAGGGGGA  CAGCGGGGGC
1321  CCGCACGTCA  CCCGCTTCAA  GGACACCTAC  TTCGTGACAG  GCATCGTCAG  CTGGGGAGAG
1381  GGCTGTGCCC  GTAAGGGGAA  GTACGGGATC  TACACCAAGG  TCACCGCCTT  CCTCAAGTGG
1441  ATCGACAGGT  CCATGAAAAC  CAGGGGCTTG  CCCAAGGCCA  AGAGCCATGC  CCCGGAGGTC
1501  ATAACGTCCT  CTCCATTAAA  GTGAGATCCC  ACTCAAAAAA  AAAAAAAAAA  AAAAAAAAAA
``` ated Factor X (FXa) inhibitors.

SEQUENCE LISTING

```
<160> NUMBER OF SEQ ID NOS: 3

<210> SEQ ID NO 1
<211> LENGTH: 488
<212> TYPE: PRT
<213> ORGANISM: Homo sapiens

<400> SEQUENCE: 1

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190
```

```
Glu Ala Pro Asp Ser Ile Thr Trp Lys Pro Tyr Asp Ala Asp Leu
            195                 200                 205

Asp Pro Thr Glu Asn Pro Phe Asp Leu Leu Asp Phe Asn Gln Thr Gln
            210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
            245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
            275                 280                 285

Gly Asp Arg Asn Thr Glu Gln Glu Glu Gly Gly Glu Ala Val His Glu
            290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
            325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
            355                 360                 365

Glu Lys Gly Arg Gln Ser Thr Arg Leu Lys Met Leu Glu Val Pro Tyr
            370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
            405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
            435                 440                 445

Tyr Gly Ile Tyr Thr Lys Val Thr Ala Phe Leu Lys Trp Ile Asp Arg
            450                 455                 460

Ser Met Lys Thr Arg Gly Leu Pro Lys Ala Lys Ser His Ala Pro Glu
465                 470                 475                 480

Val Ile Thr Ser Ser Pro Leu Lys
            485

<210> SEQ ID NO 2
<211> LENGTH: 1560
<212> TYPE: DNA
<213> ORGANISM: Homo sapiens

<400> SEQUENCE: 2
gactttgctc cagcagcctg tcccagtgag gacagggaca cagtactcgg ccacaccatg      60
gggcgcccac tgcacctcgt cctgctcagt gcctccctgg ctggcctcct gctgctcggg     120
gaaagtctgt tcatccgcag ggagcaggcc aacaacatcc tggcgagggt cacgagggcc     180
aattcctttc ttgaagagat gaagaaagga cacctcgaaa gagtgcatgg aagagacc      240 tgctcatacg aagaggcccg cgaggtcttt gaggacagcg acaagacgaa tgaattctgg     300
aataaataca agatggcga ccagtgtgag accagtcctt gccagaacca gggcaaatgt     360
aaagacggcc tcggggaata cacctgcacc tgtttagaag gattcgaagg caaaaactgt     420
```

```
gaattattca cacggaagct ctgcagcctg gacaacgggg actgtgacca gttctgccac    480
gaggaacaga actctgtggt gtgctcctgc gcccgcgggt acaccctggc tgacaacggc    540
aaggcctgca ttcccacagg gccctacccc tgtgggaaac agaccctgga acgcaggaag    600
aggtcagtgg cccaggccac cagcagcagc ggggaggccc ctgacagcat cacatggaag    660
ccatatgatg cagccgacct ggaccccacc gagaacccct cgacctgct tgacttcaac    720 cagacgcagc ctgagagggg cgacaacaac ctcaccagga tcgtgggagg ccaggaatgc    780
aaggacgggg agtgtccctg gcaggccctg ctcatcaatg aggaaaacga gggtttctgt    840
ggtggaacca ttctgagcga gttctacatc ctaacggcag cccactgtct ctaccaagcc    900
aagagattca aggtgagggt aggggaccgg aacacggagc aggaggaggg cggtgaggcg    960
gtgcacgagg tggaggtggt catcaagcac aaccggttca caaaggagac ctatgacttc    1020
gacatcgccg tgctccggct caagaccccc atcaccttcc gcatgaacgt ggcgcctgcc    1080
tgcctccccg agcgtgactg ggccgagtcc acgctgatga cgcagaagac ggggattgtg    1140
agcggcttcg ggcgcaccca cgagaagggc cggcagtcca ccaggctcaa gatgctggag    1200 gtgcccctacg tggaccgcaa cagctgcaag ctgtccagca gcttcatcat cacccagaac    1260
atgttctgtg ccggctacga caccaagcag gaggatgcct gccagggga cagcgggggc    1320 ccgcacgtca cccgcttcaa ggacacctac ttcgtgacag gcatcgtcag ctggggagag    1380
ggctgtgccc gtaaggggaa gtacgggatc tacaccaagg tcaccgcctt cctcaagtgg    1440
atcgacaggt ccatgaaaac cagggcttg cccaaggcca agagccatgc cccggaggtc    1500
ataacgtcct ctccattaaa gtgagatccc actcaaaaaa aaaaaaaaaa aaaaaaaaa    1560
```

<210> SEQ ID NO 3  
<211> LENGTH: 6  
<212> TYPE: PRT  
<213> ORGANISM: Artificial Sequence  
<220> FEATURE:  
<223> OTHER INFORMATION: Proteolytic Cleavage Site

<400> SEQUENCE: 3

Arg Lys Arg Arg Lys Arg  
1               5

COMPOSITIONS AND METHODS FOR COUNTERACTING FACTOR XA INHIBITION

CROSS-REFERENCE TO RELATED APPLICATION

This application claims the benefit of U.S. Provisional Application No. 61/759,332, filed 31 Jan. 2013, the contents of which are incorporated herein by reference in its entirety.

REFERENCE TO SEQUENCE LISTING

The Sequence Listing submitted concurrently herewith under 37 CFR § 1.821 in a computer readable form (CRF) via EFS-Web as file name PC72006_SEQLIST_ST25.txt is incorporated herein by reference. The electronic copy of the Sequence Listing was created on 17 Jan. 2018, with a file size of 6,835 bytes.

BACKGROUND OF THE INVENTION

Pharmacological anticoagulation is the mainstay of treatment for patients with prothrombotic conditions. For over fifty years, the only oral anticoagulant available was warfarin, an inhibitor of the vitamin K epoxide reductase (VKOR) that recycles oxidized vitamin K. Warfarin has many drawbacks, including unpredictable pharmacokinetics that necessitate frequent monitoring of coagulation parameters and dose adjustment. However, in the event of emergency bleeding or the need for urgent surgery, antidotes exist that allow rapid and complete reversal.

Oral direct FXa inhibitors are emerging anticoagulants that have the potential to simplify dosing schemes and hemostatic monitoring in patients with prothrombotic diseases when compared to standard treatments, such as warfarin. Although these drugs have many advantages over warfarin, no fully efficacious reversal agent is available for these novel anticoagulants.

The lack of a specific countermeasure to their effects, however, is a critical unmet clinical need that could limit the widespread adoption of these agents due to fears of unmanageable bleeding.

SUMMARY OF THE INVENTION

Applicants have addressed this critical unmet clinical need by providing compositions and methods for counteracting the effects of direct activated Factor X (FXa) inhibitors.

According to some embodiments, the disclosure provides methods for reducing or preventing bleeding in a subject being treated with a direct Factor Xa (FXa) inhibitor by administering a composition comprising a Factor Xa variant containing at least one modification including substitution for the wild-type amino acid at position 16 (using the chymotrypsin numbering system) with Thr, Leu, Phe, Asp or Gly, or substitution for the wild-type amino acid at position 17 (using the chymotrypsin numbering system) with Leu, Ala, or Gly. In certain embodiments, treatment with a composition comprising a FXa variant results in at least a 50% reduction in bleeding. According to certain embodiments, direct Factor Xa inhibitors include rivaroxaban or apixaban. In some embodiments, the plasma concentration of the direct FXa inhibitor is a typical therapeutic amount or a supratherapeutic amount. For example, in some embodiments, the plasma concentration of rivaroxaban can be about 500 nM, or greater, and the plasma concentration of apixaban can be about 250 nM, or greater. According to certain embodiments the FXa variant contains the substitution I16L. In some embodiments, the FXa variant is capable of countering the effect of the direct Factor Xa inhibitor at a plasma concentration that is at least 100-fold lower than the plasma concentration of the Factor Xa inhibitor. In certain embodiments, the composition comprising the FXa variant is administered before a planned surgery, after an injury, or after an intentional or accidental overdose with a direct FXa inhibitor. In some embodiments, hemostasis in the subject is monitored using a hemostasis assay after a first dose with a FXa variant and, if adequate hemostasis is not attained by a predetermined time, at least one second dose of FXa variant is administered to achieve sufficient hemostasis. According to some embodiments, the predetermined time is about 15 mins, 30 mins, 45 mins or 60 mins after the first dose of FXa variant is administered. Other times are also possible. In some other embodiments, at least a second procoagulant is administered in addition to FXa variant, including for example, a different FXa variant, factor IX, factor XIa, factor XIIa, factor VIII, factor VIIa, FEIBA or prothrombin complex concentrate (PCC).

According to some embodiments, the disclosure provides methods for increasing the amount of thrombin produced in response to activation of the extrinsic or intrinsic clotting pathway in a subject being treated with a direct Factor Xa (FXa) inhibitor by administering a composition comprising a Factor Xa variant containing at least one modification including substitution for the wild-type amino acid at position 16 (using the chymotrypsin numbering system) with Thr, Leu, Phe, Asp- or Gly, or substitution for the wild-type amino acid at position 17 (using the chymotrypsin numbering system) with Leu, Ala, or Gly. According to certain embodiments, direct Factor Xa inhibitors include rivaroxaban or apixaban. In some embodiments, the plasma concentration of the direct FXa inhibitor is a typical therapeutic amount or a supratherapeutic amount. For example, in some embodiments, the plasma concentration of rivaroxaban can be about 500 nM, or greater, and the plasma concentration of apixaban can be about 250 nM, or greater. According to certain embodiments the FXa variant contains the substitution I16L. According to certain embodiments, the amount of thrombin produced increases by about 5%, 10%, 15%, 20%, 30%, 40%, 50%, 60%, 70%, 80%, 90%, 100%, 150%, 200%, or more. In some embodiments, the FXa variant is capable of countering the effect of the direct Factor Xa inhibitor at a plasma concentration that is at least 100-fold lower than the plasma concentration of the Factor Xa inhibitor. In certain embodiments, the composition comprising the FXa variant is administered before a planned surgery, after an injury, or after an intentional or accidental overdose with a direct FXa inhibitor. In some embodiments, hemostasis in the subject is monitored using a hemostasis assay after a first dose with a FXa variant and, if adequate hemostasis is not attained by a predetermined time, at least one second dose of FXa variant is administered to achieve sufficient hemostasis. According to some embodiments, the predetermined time is about 15 mins, 30 mins, 45 mins or 60 mins after the first dose of FXa variant is administered. Other times are also possible. In some other embodiments, at least a second procoagulant is administered in addition to FXa variant, including for example, a different FXa variant, factor IX, factor XIa, factor XIIa, factor VIII, factor VIIa, FEIBA or prothrombin complex concentrate (PCC).

According to some embodiments, the disclosure provides methods for decreasing clotting time (as measured, for example, using PT or INR, or some other assay) in a subject being treated with a direct Factor Xa (FXa) inhibitor by administering a composition comprising a Factor Xa variant containing at least one modification including substitution for the wild-type amino acid at position 16 (using the chymotrypsin numbering system) with Thr, Leu, Phe, Asp or Gly, or substitution for the wild-type amino acid at position 17 (using the chymotrypsin numbering system) with Leu, Ala, or Gly. According to certain embodiments, direct Factor Xa inhibitors include rivaroxaban or apixaban. In some embodiments, the plasma concentration of the direct FXa inhibitor is a typical therapeutic amount or a supratherapeutic amount. For example, in some embodiments, the plasma concentration of rivaroxaban can be about 500 nM, or greater, and the plasma concentration of apixaban can be about 250 nM, or greater. According to certain embodiments the FXa variant contains the substitution I16L. According to certain embodiments, clotting time is reduced by about 5%, 10%, 15%, 20%, 30%, 40%, 50%, 60%, 70%, 80%, 90%, or more. In some embodiments, the FXa variant is capable of countering the effect of the direct Factor Xa inhibitor at a plasma concentration that is at least 100-fold lower than the plasma concentration of the Factor Xa inhibitor. In certain embodiments, the composition comprising the FXa variant is administered before a planned surgery, after an injury, or after an intentional or accidental overdose with a direct FXa inhibitor. In some embodiments, hemostasis in the subject is monitored using a hemostasis assay after a first dose with a FXa variant and, if adequate hemostasis is not attained by a predetermined time, at least one second dose of FXa variant is administered to achieve sufficient hemostasis. According to some embodiments, the predetermined time is about 15 mins, 30 mins, 45 mins or 60 mins after the first dose of FXa variant is administered. Other times are also possible. In some other embodiments, at least a second procoagulant is administered in addition to FXa variant, including for example, a different FXa variant, factor IX, factor XIa, factor XIIa, factor VIII, factor VIIa, FEIBA or prothrombin complex concentrate (PCC).

BRIEF DESCRIPTION OF THE DRAWINGS

FIGS. 8A-B show FXa$^{I16L}$ corrects whole blood clotting in the presence of rivaroxaban. Whole blood thromboelastography was used to assess the ability of FXa$^{I16L}$ to reverse the effects of rivaroxaban at a typical (A) and a high (B) dose.

FIG. 10A shows a dose response of rivaroxaban and FIG. 10B shows a dose response of FXa$^{I16L}$ in the presence of rivaroxaban.

FIG. 13A shows clot formation in an untreated mouse. FIG. 13B shows that rivaroxaban delayed and reduced platelet accumulation and prevented fibrin deposition. By contrast, FIG. 13C shows that in a mouse administered rivaroxaban and FXa$^{I16L}$ clot formation occurred at the site of injury.

FIG. 14 is the amino acid sequence of wild-type human Factor X preprotein (SEQ ID NO:1). The signal peptide corresponds to amino acids 1-23. The propeptide corresponds to amino acids 24-40. The mature light chain of activated Factor X (FXa) corresponds to amino acids 41-179. The mature heavy chain of activated FXa (after removal of the activation peptide) corresponds to amino acids 235-488. The activation peptide (AP) corresponds to amino acids 183-234.

FIG. 15 is the nucleotide sequence of the cDNA encoding wild-type human Factor X preprotein (SEQ ID NO:2). The coding sequence corresponds to nucleotides 58 to 1524.

DETAILED DESCRIPTION

Figure 1A:
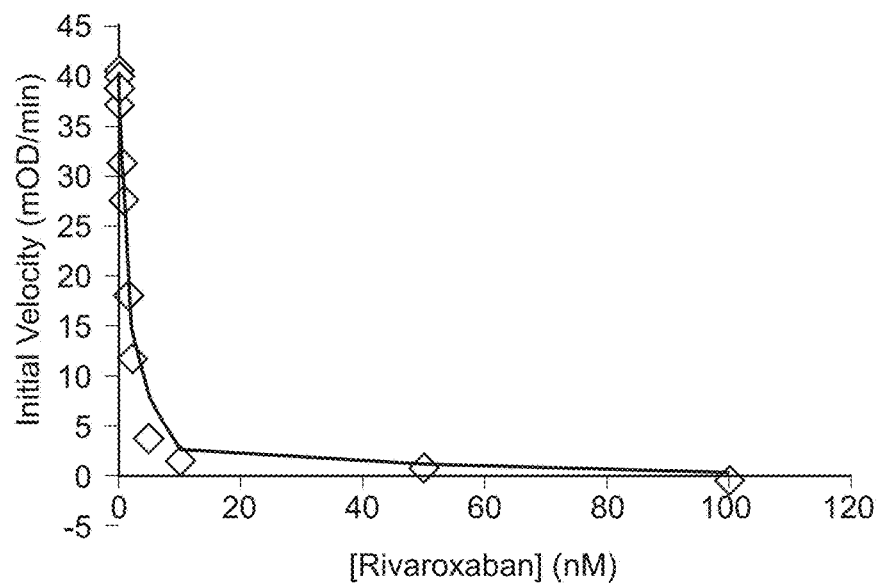
FIGS. 1A-B show inhibition of free wt-FXa or FXa$^{I16L}$ by rivaroxaban. The initial velocity of peptidyl substrate (SpecXa; 200 uM) hydrolysis by A) wt-FXa (2 nM) or B) FXa$^{I16L}$ (6 nM) was determined at increasing concentrations of rivaroxaban. The Ki value is given on each graph.

The disclosure provides compositions and methods for counteracting the anti-coagulant effect of a direct FXa inhibitor in a subject in need thereof. Applicants have discovered that certain FXa variants rapidly and completely counteract the effect of a direct FXa inhibitor in a dose dependent manner. More specifically, applicants have discovered that a relatively small amount of an FXa variant restores normal coagulation activity in vivo in the presence of FXa inhibitor at therapeutic concentrations and even at supratherapeutic concentrations. By providing fast and effective antidotes for the anti-coagulation effects of direct FXa inhibitors, Applicants' disclosure therefore contributes to fulfilling the promise of these advantageous anti-coagulants.

Coagulation factor X (FX) is a zymogen which, upon activation by the intrinsic factor IX/factor VIII or extrinsic pathway (tissue factor/factor VIIa), becomes FXa, which is the protease moiety of prothrombinase. Following proteolytic cleavage of the Arg-Ile scissile bond, releasing an activation peptide (AP), a series of well defined structural changes in the zymogen drives the activation process to the mature active serine protease (See Toso et al., (2008) *J. Biol. Chem.* 283, 18627-18635; Bunce et al., (2011) *Blood* 117, 290-298; and Ivanciu et al., (2011) *Nat. Biotechnol.* 29, 1028-1033, incorporated by reference herein in their entirety). The mature FXa has a light chain and a heavy chain that contains the catalytic domain. The mature FXa becomes an active serine protease upon formation of the prothrombinase complex, which includes binding of an activated cofactor, Factor Va (FVa).

Variant forms of FX have been developed that upon activation cleavage yield a zymogen-like FXa variant. That is, once cleaved, the resulting FXa variant has poor active site function and is more resistant to inactivation by circulating inhibitors (i.e. antithrombin III and TFPI). The FXa variants, thus, have longer half-lives in plasma than wild-type FXa. The FXa variant binds FVa, lipid membrane and calcium to form a fully active prothrombinase complex that efficiently activates prothrombin.

The zymogen-like variants of FXa circulate in the zymogen-like conformation and do not seem to be thrombogenic (See Toso et al., (2008) *J. Biol. Chem.* 283, 18627-18635 and Ivanciu et al., (2011) *Nat. Biotechnol.* 29, 1028-1033, incorporated by reference herein in their entirety). Examples of such FXa variants are described in International patent publication WO2007/059513, incorporated herein by reference in its entirety.

The enzymes of coagulation are trypsin-like enzymes that belong to the S1 peptidase family of proteases that bear a chymotrypsin-like fold. The coagulation proteases contain catalytic domains that are highly homologous to each other and to the ancestral serine proteases of digestion. The structural homology/identity is so great (>70%) that residues in the catalytic domains of the coagulation enzymes (including Factor Xa) are numbered according to the corresponding residues in chymotrypsinogen. (Chymotrypsin numbering system; see Bajaj and Birktoft, Methods Enzymol. 1993; 222:96-128, Table 2, and Bode W, Mayr I, Bauman Y, et al. The refined 1.9 Å crystal structure of human alpha-thrombin: interaction with D-Phe-Pro-Arg chloromethylketone and significance of the Tyr-Pro-Trp insertion segment. EMBO J 1989; 8(11):3467-3475, both of which are incorporated by reference herein in their entireties). Accordingly, amino acids may be referred to herein according to the chymotrypsin numbering system, which is well-known to those of skill in the art.

According to the disclosure, an FXa variant may be an FXa protein comprising an amino acid substitution that makes the variant more zymogen-like compared to a wild-type FXa protein in vivo or in vitro. FXa variants of the disclosure substantially regain wild-type FXa activity upon formation of prothrombinase. Examples of FXa variants that are useful in methods of the disclosure are variants comprising a modification selected from the group consisting of: a) Ile at position 16 is Thr, Leu, Phe, Asp or Gly and b) Val at position 17 is Leu, Ala, or Gly, according to the chymotrypsin numbering system. Amino acids 16 and 17 in the chymotrypsin numbering system occur at amino acids 235 and 236, respectively, of SEQ ID NO:1 (human Factor X preproprotein). In certain embodiments, FXa variants are $FXa^{I16L}$ and $FXa^{I16T}$ (the nomenclature used herein for the FXa variants recites the original amino acid at the numbered position according to the chymotrypsin numbering system followed by the substituted amino acid). The FXa variants can be variants of any mammalian FXa. Of particular interest, however, are FXa variants of human FXa.

In certain embodiments, the FX variant that is activated into a variant FXa of the disclosure may be further modified by inserting a non-native intracellular proteolytic cleavage site. In a non-limiting example, to express "activated" zymogen-like FXa variants in mammalian cells, a non-native intracellular proteolytic cleavage site can be inserted between the Arg at position 234 of SEQ ID NO:1 (position 15 in the chymotrypsin numbering system) and the amino acid at the position corresponding to position 235 of SEQ ID NO:1 (position 16 in the chymotrypsin numbering system) in the variant FX zymogen. In certain embodiments, the non-native intracellular protease cleavage site is Arg-Lys-Arg or Arg-Lys-Arg-Arg-Lys-Arg (SEQ ID NO:3). These cleavage sites are efficiently recognized by proteases (PACE/furin-like enzymes) within the cell and are removed. This cleavage may result in a processed variant FXa in which the mature heavy chain of the molecule now begins at the amino acid at the position corresponding to position 235 of SEQ ID NO:1 (position 16 in the chymotrypsin numbering system). Introduction of this cleavage site at said position allows for the intracellular conversion of FX to FXa.

In certain embodiments the entire amino acid sequence of the FX variant activation peptide (AP) (i.e., amino acids 183-234 of SEQ ID NO:1) is replaced with a non-native intracellular protease cleavage site. According to certain embodiments, the non-native intracellular protease cleavage site is Arg-Lys-Arg or Arg-Lys-Arg-Arg-Lys-Arg (SEQ ID NO:3). As explained above, this modification allows for intracellular cleavage of the FX variant expressed by cells. The intracellular cleavage converts FX variant to activated zymogen-like FXa variant which is then secreted by cells for subsequent purification. This approach obviates the need for extracellular cleavage that would otherwise be required to activate the variant clotting factor, for example, after isolating the protein or just before blood clotting.

In certain embodiments, FXa variants of the disclosure are derived from FX variant preproteins comprising native wild-type human signal sequence and/or propeptide sequence. In other embodiments, FX signal sequences and/or propeptide from non-human species can be used in place of the corresponding native amino acid sequences. And in yet other embodiments, signal sequence and/or propeptide sequence from other human or non-human secreted proteins can be used in place of the corresponding native amino acid sequences.

In an exemplary embodiment, a FXa variant comprises amino acids 41-179 and amino acids 235-488 of SEQ ID NO:1, wherein the amino acid at position 235 (isoleucine in the wild-type sequence) is substituted with a different amino acid selected from the group consisting of threonine (Thr), leucine (Leu), phenylalanine (Phe), aspartic acid (Asp), or glycine (Gly). These substitutions can respectively be written using the nomenclature I235T, I235L, I235F, I235D and I235G, where the first letter is the single letter code for isoleucine and the last letter is the single letter code for the amino acid being substituted into the wild-type sequence. Because position 235 of SEQ ID NO:1 is equivalent to position 16 in the chymotrypsin numbering system, the same substitutions can be written I16T, I16L, I16F, I16D and I16G. In an embodiment, a FXa variant comprises amino acids 41-179 and amino acids 235-488 of SEQ ID NO:1, wherein the amino acid at position 235 is substituted with Thr (i.e., I235T or I16T). In an embodiment, a FXa variant comprises amino acids 41-179 and amino acids 235-488 of SEQ ID NO:1, wherein the amino acid at position 235 is substituted with Leu (i.e., I235L or I16L). In an embodiment, a FXa variant comprises amino acids 41-179 and amino acids 235-488 of SEQ ID NO:1, wherein the amino acid at position 235 is substituted with Phe (i.e., I235F or I16F). In an embodiment, a FXa variant comprises amino acids 41-179 and amino acids 235-488 of SEQ ID NO:1, wherein the amino acid at position 235 is substituted with Asp (i.e., I235D or I16D). In an embodiment, a FXa variant comprises amino acids 41-179 and amino acids 235-488 of SEQ ID NO:1, wherein the amino acid at position 235 is substituted with Gly (i.e., I235G or I16G).

According to another exemplary embodiment, a FXa variant comprises amino acids 41-179 and amino acids 235-488 of SEQ ID NO:1, wherein the amino acid at position 236 (valine in the wild-type sequence) is substituted with a different amino acid selected from the group consisting of leucine (Leu), alanine (Ala), or glycine (Gly). These substitutions can respectively be written using the nomenclature V236L, V236A, and V236G, where the first letter is the single letter code for valine and the last letter is the single letter code for the amino acid being substituted into the wild-type sequence. Because position 236 of SEQ ID NO:1 is equivalent to position 17 in the chymotrypsin numbering system, the same substitutions can be written V17L, V17A, and V17G. In an embodiment, a FXa variant comprises amino acids 41-179 and amino acids 235-488 of SEQ ID NO:1, wherein the amino acid at position 236 is substituted with Leu (i.e., V236L or V17L). In an embodiment, a FXa variant comprises amino acids 41-179 and amino acids 235-488 of SEQ ID NO:1, wherein the amino acid at position 236 is substituted with Ala (i.e., V236A or V17A). In an embodiment, a FXa variant comprises amino acids 41-179 and amino acids 235-488 of SEQ ID NO:1, wherein the amino acid at position 236 is substituted with Gly (i.e., V236G or V17G).

In other embodiments, FXa variants of the disclosure, including those specific variants described in the preceding paragraphs, can include various isoforms of the light and/or mature heavy chain of the protein. Non-limiting exemplary isoforms of the FXa variant mature heavy chain include the alpha and beta versions of the mature heavy chain. Jesty et al., J Biol Chem. 1975 Jun. 25; 250(12):4497-504, incorporated by reference herein. Compositions of the disclosure can include FXa variant proteins in which one or the other or both alpha and beta mature heavy chain isoforms are represented.

According to yet other embodiments, isoforms of FXa variant proteins, including those specific variants described in the preceding paragraphs, can include isoforms in which a variable number of amino acids (for example, 1, 2, 3, 4, 5, 6, or more amino acids) are either missing from or added to the carboxy terminus of the light chain and/or mature heavy chains of the protein.

According to certain embodiments, FXa variants of the disclosure include proteins with a certain minimal degree of homology or sequence identity compared to the amino acid sequence of wild-type FXa in SEQ ID NO:1. Thus, for example, FXa variants include proteins that contain a light and mature heavy chain that are at least 60%, 70%, 80%, 85%, 90%, 95%, 98%, or 99% homologous or identical in sequence with the wild-type FXa light and mature heavy chains in SEQ ID NO:1, wherein such FXa variants also include a substitution at the amino acid position corresponding to position 235 of SEQ ID NO:1 with Thr, Leu, Phe, Asp, or Gly, or a substitution at the amino acid position corresponding to position 236 of SEQ ID NO:1 with Leu, Ala, or Gly, and further wherein such FXa variants are zymogenic until incorporated into prothrombinase complex. In the amino acid sequence of SEQ ID NO:1, the wild-type FXa light chain sequence corresponds to amino acids 41 to 179 and the wild-type FXa mature heavy chain sequence corresponds to amino acids 235 to 488. Percentage amino acid sequence homology or identity can readily be determined using software such as Protein BLAST available at the website of the National Center for Biotechnology Information (http://blast.ncbi.nlm.nih.gov/Blast.cgi).

According to other non-limiting embodiments, FXa variants of the disclosure can also include FXa variants containing one or more post-translational modifications including, without limitation, one or more O-linked or N-linked carbohydrate groups or a variable number of gamma-carboxyglutamic acid (Gla) residues. FXa variants of the disclosure can further include chemically modified FXa variant proteins. Other FXa variants useful in the methods of the disclosure are also possible.

As used herein, the term $FXa^{I16x}$ refers to a variant of activated Factor X wherein the amino acid corresponding to position 235 in SEQ ID NO:1 (corresponding to position 16 in the chymotrypsin numbering system) is changed from the amino acid in the wild-type sequence (isoleucine) to a different amino acid denoted "x". In some non-limiting exemplary embodiments, amino acid "x" can be threonine (Thr or T), leucine (Leu or L), phenylalanine (Phe or F), aspartic acid (Asp or D), or glycine (Gly or G).

As used herein, the term $FXa^{V17y}$ refers to a variant of activated Factor X wherein the amino acid corresponding to position 238 in SEQ ID NO:1 (corresponding to position 17 in the chymotrypsin numbering system) is changed from the amino acid in the wild-type sequence (valine) to a different amino acid denoted "y". In some non-limiting exemplary embodiments, amino acid "y" can be leucine (Leu or L), alanine (Ala or A), or glycine (Gly or G).

The terms $FXa^{I16x}$ and $FXa^{V17y}$ are not limited by the protein sequence set forth in SEQ ID NO:1. Rather these terms additionally include the variety of isoforms and homologous proteins described herein with the specified substitution mutations at positions 16 or 17 in the chymotrypsin numbering system that behave as zymogens until incorporated into prothrombinase complex.

An FXa variant of the disclosure may be produced by any technique for expressing a protein.

An "isolated protein," "isolated polypeptide" or "isolated variant" is a protein, polypeptide or variant that by virtue of its origin or source of derivation (1) is not associated with naturally associated components that accompany it in its native state, (2) is free of other proteins from the same species, (3) is expressed by a cell from a different species, or (4) does not occur in nature. Thus, a polypeptide that is chemically synthesized or synthesized in a cellular system different from the cell from which it naturally originates will be "isolated" from its naturally associated components. A protein may also be rendered substantially free of naturally-associated components by isolation, using protein purification techniques well known in the art.

A protein or polypeptide is "substantially pure," "substantially homogeneous," or "substantially purified" when at least about 60 to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and may be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The methods of the disclosure are useful to counteract a direct FXa inhibitor. A direct FXa inhibitor is an inhibitor that binds directly to FXa and selectively binds FXa over other proteases. Direct FXa inhibitors are noncompetitive inhibitors of FXa with respect to prothrombin. They bind the substrate binding cleft and inhibit FXa competitively with respect to small peptide substrates that also bind this region. They inhibit FXa with high picomolar affinity and are highly protein bound in plasma. Examples of direct FXa inhibitors are rivaroxaban, apixaban, betrixaban, darexaban, edoxaban and otamixaban. In certain embodiments, direct FXa inhibitors are selected from rivaroxaban and apixaban.

According to the disclosure, an FXa variant can be used to counteract a direct FXa inhibitor that binds FXa or that binds FXa that has formed prothrombinase. The direct FXa inhibitors may or may not require cofactors of FXa for inhibition. According to the methods of the disclosure, an FXa variant, such as $FXa^{I16L}$ and $FXa^{I16T}$, are administered to a subject whose blood contains a direct FXa inhibitor.

The disclosure encompasses the use of a FXa variant to counteract direct FXa inhibitors, including but not limited to synthetic inhibitors, small molecule inhibitors, orally available inhibitors, or reversible inhibitors. The FXa inhibitor may be any combination of these features, such as an orally available, synthetic, reversible, small molecule inhibitor. In certain embodiments, the direct FXa inhibitors may be selected from rivaroxaban, apixaban, betrixaban, darexaban, edoxaban and otamixaban (see Perzborn et al., Nat Rev Drug Discov. 2011 January; 10(1):61-75; Turpie, Arterioscler Thromb Vasc Biol. 2007 June; 27(6):1238-47; Pinto et al., Expert Opin. Ther. Patents 22:645-661 (2012); Pinto, et al., J. Med. Chem. 50:5339-5356 (2007), each of which is incorporated by reference herein). In certain embodiments, direct FXa inhibitors are selected from rivaroxaban or apixaban.

In some embodiments, a FXa variant of the disclosure can be administered to a subject to reverse the effects of a direct FXa inhibitor where such inhibitor occurs at therapeutic concentrations. In other embodiments, a FXa variant of the disclosure can be administered to a subject to reverse the effects of a direct FXa inhibitor where such inhibitor occurs at supratherapeutic concentrations. A supratherapeutic concentration is one that is higher than that ordinarily considered required to safely achieve anti-coagulation in a particular subject or class of subjects. Supratherapeutic concentrations of a direct FXa inhibitor can result from accidental or intentional overdose. Supratherapeutic concentrations of a direct FXa inhibitor can also result from unexpected effects in particular subjects, such as an unexpectedly high sensitivity to these drugs, or unexpectedly slow rate of clearance, due for example to drug interactions or other factors. Determination of what would be a therapeutic concentration or supratherapeutic concentration of direct FXa inhibitor in a particular subject or class of subjects is within the knowledge of those ordinarily skilled in the art.

According to the disclosure, an FXa variant is used to counteract a direct FXa inhibitor or inhibitors that selectively bind FXa over other trypsin-like proteases by at least 5-fold, at least 6-fold, at least 7-fold, at least 10-fold, at least 15-fold, at least 20-fold, at least 25-fold, at least 30-fold, at least 50-fold, at least 100-fold, at least, 500-fold, at least 1,000-fold, at least 5,000-fold or at least 10,000-fold.

The direct FXa inhibitor may bind an FXa variant with a $K_i$ of about $2\times10^{-7}$ M or less. "$K_i$" refers to the inhibitor constant of a particular inhibitor-target interaction, which is the concentration required to produce half maximum inhibition. One can determine the $K_i$ by using methods known in the art. The disclosure contemplates, thus, counteracting a direct. FXa inhibitor that binds an FXa variant free of the prothrombinase complex with a $K_i$ of about $2\times10^{-8}$ M or less, about $1\times10^{-8}$ M or less, about $9\times10^{-9}$ M or less, about $8\times10^{-9}$ M or less, about $7\times10^{-9}$ M or less, about $6\times10^{-9}$M or less, about $5\times10^{-9}$ M or less, about $4\times10^{-9}$ M or less, about $3\times10^{-9}$ M or less, about $2\times10^{-9}$ M or less, about $1\times10^{-9}$ M or less, about $9\times10^{-10}$ M or less, about $8\times10^{-10}$ M Or less, about $7\times10^{-10}$ M or less, about $6\times10^{-10}$ M or less, about $5\times10^{-10}$ M or less, about $4\times10^{-10}$ M or less, about $3\times10^{-10}$ M or less, about $2\times10^{-10}$ M or less, about $1\times10^{-10}$ M or less, about $9\times10^{-11}$ M or less, about $8\times10^{-11}$ M or less, about $7\times10^{-11}$M or less, about $6\times10^{-11}$ M or less, about $5\times10^{-11}$ M or less, about $4\times10^{-10}$ M or less, about $3\times10^{-11}$ M or less, about $2\times10^{-11}$ M or less, about $1\times10^{-11}$M or less, about $9\times10^{-12}$ M or less, about $8\times10^{-12}$ M or less, about $7\times10^{-12}$ M or less, about $6\times10^{-12}$ M or less, about $5\times10^{-12}$ M or less, about $4\times10^{-12}$ M or less, about $3\times10^{-12}$ M or less, about $0.2\times10^{-12}$M or less, or about $1\times10^{-12}$ M or less, or less. The direct FXa inhibitor to be counteracted by an FXa variant according to the methods of the disclosure may bind a wild-type FXa with a $K_i$ at least 1.5 fold, at least 2-fold, at least 3-fold, at least 4-fold, at least 5-fold, at least 6-fold, at least 7-fold, at least 10-fold, at least 15-fold, at least 20-fold, at least 25-fold, at least 30-fold, or at least 50-fold less than it binds the FXa variant. The direct FXa inhibitor may bind a wild-type FXa with a $K_i$ of at least 20%, at least 30%, at least 40%, at least 50%, at least 60%, at least 70%, at least 80%, at least 90%, at least 95%, or at (east 99% less than the $K_i$ with an FXa variant free of the prothrombinase complex. The direct FXa inhibitor may bind a prothrombinase complex comprising a wild-type FXa with about the same $K_i$ as it binds a prothrombinase complex comprising an FXa variant.

In one aspect, the disclosure provides methods for counteracting the effects of a direct FXa inhibitor in a subject who is bleeding (internally or externally) or is at risk of bleeding (e.g., in the course of a planned surgery) by administering a FXa variant. In some embodiments, the direct FXa inhibitor may be present in the subject at a therapeutic concentration or a higher concentrations (i.e., a supratherapeutic concentration). In some embodiments, the therapeutic concentration may be an overdose in sensitive individuals. The methods of the disclosure, thus, are useful for providing an antidote to an overdose of a direct FXa inhibitor. In various embodiments, the subject of treatment may be a human or a veterinary subject.

Direct inhibitor overdose can be detected based on existence of symptoms or signs of excessively reduced clotting ability. Non-limiting examples include evidence of gastrointestinal bleeding, including dark tarry stools, bloody stools, and vomiting of blood. Other examples include nosebleeds, and increased tendency to, or severity of, bruising or bleeding from minor cuts and scrapes.

In a clinical setting, direct inhibitor overdose can be detected directly or by measuring the ability of subject blood to clot and detecting deviations from the expected degree of anti-coagulation. Blood clotting potential can be measured in ways familiar to those ordinarily skilled in the art. For example, overdose may be suspected when a subject's prothrombin time is excessively prolonged. In certain embodiments, overdose is confirmed when the prothrombin time expressed as an International Normalized Ratio (INR) is measured to be greater than about 1.0, 1.5, 2.0, 2.5, 3.0, 3.5, 4.0, 4.5, 5.0, 5.5, 6.0, 6.5, 7.0, 7.5, 8.0, 8.5, 9.0, 915, 10, 12, 14, 16, 18, 20, or greater.

The FXa variant may be administered whenever it is desired to counteract the effects of the direct FXa inhibitor, including but not limited to before a planned surgery, after an injury resulting in external or internal bleeding or after a direct FXa inhibitor overdose. According to the disclosure, the FXa variant may be administered at least about 12 hours, at least about 6 hours, at least about 3 hours, at least about 2 hours, at least about 1 hour, at least about 30 minutes, at least about 10 minutes, or at least about 5 minutes of when the desired counteracting effect is needed, such as before a planned surgery, after an injury resulting in external or internal bleeding or after a direct FXa inhibitor overdose.

According to another embodiment, the disclosure provides a method of administering a FXa variant to effect the urgent reversal of acquired coagulopathy due to FXa inhibition therapy in a subject with acute major bleeding. In some embodiments, subjects are adult human patients: In other embodiments, subjects are pediatric human patients.

In some embodiments, acute major bleeding is caused by trauma. In other embodiments, acute major bleeding occurs during surgery or other type of interventional procedure. Exemplary non-limiting interventional procedures include incisions, drainage, vascular surgery, appendectomy, herniotomy or hernioplasty, abdominal surgery, cholecystectomy, trephination (burr hole), lumbar puncture, cardiac pacemaker insertion, hip fracture surgery, and others. In yet other embodiments, acute major bleeding can be spontaneous bleeding with no apparent cause.

Without limitation, sites of acute major bleeding include gastrointestinal bleeding, subcutaneous or intramuscular bleeding, bladder bleeding, hemarthrosis, subdural hematoma, nasal bleeding, peritoneal bleeding, uterine bleeding, and other sites of bleeding.

Effective treatment with FXa variants of the disclosure can reverse the effects of a direct FXa inhibitor. Successful reversal of such effects by a FXa variant can be determined in a variety of ways and be measured or monitored using different assays, methods, or endpoints.

In some embodiments, treatment with a FXa variant to reverse the effects of a direct FXa inhibitor is monitored using tests or assays performed on blood or plasma from a subject treated with FXa variant. A blood sample can be taken from a subject at a predetermined time after treatment with FXa variant. The blood, or plasma prepared from it, is then subjected to one or more tests to determine if certain hemostatic pharmacodynamic parameters have been normalized despite the presence of direct FXa inhibitor. If normalization is found then the subject need not be further treated with FXa variant. If normalization is not found, however, then further treatment with FXa variant in accordance with the methods of the disclosure may be required to reverse the effect of a direct FXa inhibitor. Tests for monitoring the effectiveness of treatment with a FXa variant include tests that directly or indirectly measure the ability to clot or that measure the activity of a direct FXa inhibitor. Non-limiting exemplary tests include prothrombin time or the related International Normalized Ratio, the prothrombinase-induced clotting time assay, thromboelastometry, thromboelastography, chromogenic anti-FXa assay, thrombin generation assay, level of prothrombin fragment 1+2, level of thrombin-antithrombin III complex, activated partial thromboplastin time, and partial thromboplastin time. Other tests are also possible within the knowledge of those of ordinary skill in the art.

According to some embodiments, reversing the effects of a direct FXa inhibitor in a subject by administering a FXa variant reduces bleeding in the subject. In some embodiments, treatment with FXa variant reduces bleeding in a subject at least 10%, 20%, 30%, 40%, 50%, 60%, 70%, 80%, 90%, 95%, or 99% in the presence of a direct FXa inhibitor compared to absence of treatment with FXa variant. In other embodiments, treatment with FXa variant reduces bleeding in a subject about 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, or 95%-100%.

According to some embodiments, reversing the effects of a direct FXa inhibitor in a subject by administering a FXa variant reduces the activity of a direct FXa inhibitor in the subject. In some embodiments, treatment with FXa variant reduces activity of the direct FXa inhibitor in a subject at least 10%, 20%, 30%, 40%, 50%, 60%, 70%, 80%, 90%, 95%, or 99% in the presence of a direct FXa inhibitor compared to absence of treatment with FXa variant. In other embodiments, treatment with FXa variant reduces the activity of a direct FXa inhibitor in a subject about 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, or 95%-100%.

Activity of a direct FXa inhibitor can be monitored using a chromogenic anti-FXa assay, such as that described in Asmis, et al., Thromb Res., 129:492-498 (2012), or Barrett, et al., Thromb Haemost. 104:1263-71 (2010), each of which are incorporated by reference herein.

According to some embodiments, reversing the effects of a direct FXa inhibitor in a subject by administering a FXa variant increases the amount of thrombin produced in the blood or plasma of the subject. In some embodiments, treatment with FXa variant increases thrombin production in a subject at least 10%, 20%, 30%, 40%, 50%, 60%, 70%, 80%, 90%, 95%, 100%, 1.5 fold, 2-fold, 3-fold, 4-fold, 5-fold, 6-fold, 7-fold, 10-fold, 15-fold, 20-fold, 25-fold, 30-fold, at least 50-fold, or more in the presence of a direct FXa inhibitor compared to the absence of an FXa variant. Thrombin production in the blood or plasma of a subject can be determined using the thrombin generation assay (TGA) or other technique familiar to those of ordinary skill in the art.

According to some embodiments, reversing the effects of a direct FXa inhibitor in a subject by administering a FXa variant increases clotting in the subject. In some embodiments, treatment with FXa variant increases clotting in a Subject at least 10%, 20%, 30%, 40%, 50%, 60%, 70%, 80%, 90%, 95%, 100%, 1.5 fold, 2-fold, 3-fold, 4-fold, 5-fold, 6-fold, 7-fold, 10-fold, 15-fold, 20-fold, 25-fold, 30-fold, at least 50-fold, or more in the presence of a direct FXa inhibitor compared to the absence of an FXa variant.

According to some embodiments, reversing the effects of a direct FXa inhibitor in a subject by administering a FXa variant reduces clotting time in the subject. In some embodiments, treatment with FXa variant reduces clotting time in a subject at least 10%, 20%, 30%, 40%, 50%, 60%, 70%, 80%, 90%, 95%, or 99% in the presence of a direct FXa inhibitor compared to absence of treatment with FXa variant. In other embodiments, treatment with FXa variant reduces clotting time in a subject about 5%-10%, 10%-15%, 15%-20%, 20%-25%, 25%-30%, 30%-35%, 35%-40%, 40%-45%, 45%-50%; 50%-55%, 55%-60%, 60%-65%, 65%-70%, 70%-75%, 75%-80%, 80%-85%, 85%-90%, 90%-95%, or 95%-100%.

According to some embodiments, clotting time is determined by measuring the subject's prothrombin time (PT) which decreases as hemostasis is restored. PT is the amount of time it takes for serum to clot after addition of tissue factor. PT therefore measures the capability of the extrinsic clotting system to support clotting. PT can vary depending on the particular reagents a lab uses to run the test, but a normal PT is about 11 to 13 seconds. Clotting time can also be expressed using the International Normalized Ratio (INR), which eliminates lab to lab variability in clotting time measurements. Using the INR, a ratio of 0.8 to 1.1 indicates normal clotting. PT or INR can be determined at a predetermined time after a FXa variant is administered to a subject in need of reversal of the effects of a direct FXa inhibitor.

In some embodiments, treatment with a FXa variant to reverse the effects of a direct FXa inhibitor reduces the PT of a subject to about 25 seconds, 24 seconds, 23 seconds, 22 seconds, 21 seconds, 20 seconds, 19 seconds, 18 seconds, 17 seconds, 16 seconds, 15 seconds, 14 seconds, 13 seconds, 12 seconds, 11 seconds, 10 seconds, or less. In other embodiments, treatment with a FXa variant reduces the INR or a subject to about 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, or less. According to other embodiments, treatment with FXa variant reduces PT or INR in a subject about 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, or 95%-100%.

Prothrombin time can be measured at a predetermined after administration of a FXa variant. Thus, in some non-limiting embodiments, PT is measured 15 mins, 20 mins, 30 mins, 40 mins, 45 mins, 50 mins, 60 mins or more after administration of FXa. Other times are also possible according to the knowledge of those of ordinary skill in the art.

Clotting time can also be measured using the One-step prothrombinase-induced clotting time (PiCT) assay as described in Graff, et al., Monitoring effects of direct FXa-inhibitors with a new one-step prothrombinase-induced clotting time (PiCT) assay: comparative in vitro investigation with heparin, enoxaparin, fondaparinux and DX 9065a, Int J Clin Pharmacol Ther., 45:237-43 (2007) and Harder, et al., Monitoring direct FXa-inhibitors and fondaparinux by Prothrombinase-induced. Clotting Time (PiCT): relation to FXa-activity and influence of assay modifications, Thromb Res., 123:396-403 (2008), each of which are incorporated by reference.

In yet other embodiments, the methods of thromboelastometry or thromboelastography may be used to analyze clot formation or clotting time.

According to some embodiments, reversing the effects of a direct FXa inhibitor in a subject by administering a FXa variant increases the level of prothrombin fragment 1+2 (PF1+2) in the blood or plasma of the subject. In some embodiments, treatment with FXa variant increases PF1+2 in a subject at least 10%, 20%, 30%, 40%, 50%, 60%, 70%, 80%, 90%, 95%, 100%, 1.5-fold, 2-fold, 3-fold, 4-fold, 5-fold, 6-fold, 7-fold, 10-fold, 15-fold, 20-fold, 25-fold, 30-fold, at least 50-fold, or more in the presence of a direct FXa inhibitor compared to the absence of an FXa variant.

According to some embodiments, reversing the effects of a direct FXa inhibitor in a subject by administering a FXa variant increases the level of thrombin-antithrombin III complex (TAT) in the blood or plasma of the subject. In some embodiments, treatment with FXa variant increases TAT in a subject at least 10%, 20%, 30%, 40%, 50%, 60%, 70%, 80%, 90%, 95%, 100%, 1.5-fold, 2-fold, 3-fold, 4-fold, 5-fold, 6-fold, 7-fold, 10-fold, 15-fold, 20-fold, 25-fold, 30-fold, at least 50-fold, or more in the presence of a direct FXa inhibitor compared to the absence of an FXa variant.

According to some embodiments, reversing the effects of a direct FXa inhibitor in a subject by administering a FXa variant reduces activated partial thromboplastin time (aPTT) in the subject. In some embodiments, treatment with FXa variant reduces activated partial thromboplastin time (aPTT) in a subject at least 10%, 20%, 30%, 40%, 50%, 60%, 70%, 80%, 90%, 95%, or 99% in the presence of a direct FXa inhibitor compared to absence of treatment with FXa variant. In other embodiments, treatment with FXa variant reduces aPTT in a subject about 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, or 95%-100%.

According to some embodiments, reversing the effects of a direct FXa inhibitor in a subject by administering a FXa variant reduces partial thromboplastin time (PTT) in the subject. In some embodiments, treatment with FXa variant reduces partial thromboplastin time (PTT) in a subject at least 10%, 20%, 30%, 40%, 50%, 60%, 70%, 80%, 90%, 95%, or 99% in the presence of a direct FXa inhibitor compared to absence of treatment with FXa variant. In other embodiments, treatment with FXa variant reduces PTT in a subject about 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, or 95%-100%.

In other embodiments, clinical endpoints can be relied upon to determine if hemostasis has been adequately restored in a subject treated with a FXa variant to reverse the effects of a direct FXa inhibitor. For example, where a subject presents with acute bleeding, clinical hemostatic efficacy can be scored "very good" where prompt cessation of existing bleeding occurs after treatment with FXa variant; "satisfactory" where there is a 1-2 hr delay in bleeding cessation; "questionable" where there is a >2 hr delay in bleeding cessation; and "none" where an effect on bleeding is absent. Where treatment with FXa variant is determined to be less than satisfactory, then an additional dose of FXa variant can be administered to effect adequate hemostasis. In a further example, where a subject is undergoing an interventional procedure, clinical hemostatic efficacy can be scored "very good" where normal hemostasis is attained during the procedure; "satisfactory" where intraprocedural hemostasis is mildly abnormal as judged by quantity or quality of blood loss (e.g., slight oozing); "questionable"

where intraprocedural hemostasis is moderately abnormal as judged by quantity or quality of blood loss (e.g., controllable bleeding); and "none" where intraprocedural hemostasis is severely abnormal as judged by quantity or quality of blood loss (e.g., severe refractory hemorrhage).

A therapeutically effective dose of a direct FXa inhibitor depends upon numerous factors that are well known to a medical practitioner of skill in the art. A typical therapeutic plasma concentration of rivaroxaban is about 500 nM. However, according to the disclosure, an FXa variant can be administered to counteract lower or higher concentrations of inhibitor. The plasma concentration of rivaroxaban in a subject to be treated with an FXa variant may be lower or higher than the typical therapeutic concentration, for example about 100 nM, about 200 nM, about 300 nM, about 400 nM, about 500 nM, about 600 nM, about 700 nM, about 800 nM, about 900 nM or about 1,000 nM.

A typical therapeutic plasma concentration of apixaban is about 250 nM. In certain embodiments, the FXa variant is administered to a subject with a plasma concentration of apixaban of about 100 nM, about 200 nM, about 300 nM, about 400 nM, about 500 nM, about 600 nM, about 700 nM, about 800 nM, about 900 nM or about 1,000 nM.

Likewise, according to the disclosure, an FXa variant can be used to counteract a direct FXa inhibitor in cases of overdose, such as when the plasma concentration of the inhibitor is at least 20%, at least 30%, at least 40%, at least 50%, at least 60%, at least 70%, at least 80%, at least 90%, at least 95%, at least 99%, or at least 1.5 fold, at least 2-fold, at least 3-fold, at least 4-fold, at least 5-fold, at least 6-fold, at least 7-fold, at least 10-fold, at least 15-fold, at least 20-fold, at least 25-fold, at least 30-fold, or at least 50-fold higher than the typical therapeutic plasma concentration.

The FXa variants are surprisingly effective in counteracting a direct FXa inhibitor at a plasma concentration that is lower than the plasma concentration of the direct FXa inhibitor. According to the disclosure, the FXa variant counters the effect of a direct FXa inhibitor at a plasma concentration ratio of variant to inhibitor of about 1 to 10, about 1 to 25, about 1 to 50, about 1 to 100, about 1 to 250, about 1 to 500, about 1 to 1,000, about 1 to 2,500, about 1 to 5,000 or about 1 to 10,000. In certain embodiments, the FXa variant counters the effect of a direct FXa inhibitor at a plasma concentration of at least 10-fold, at least 25-fold, at least 50-fold, at least 100-fold, at least 250-fold, at least 500-fold, at least 1,000-fold, at least 2,500-fold, at least 5,000-fold, or at least 10,000-fold lower than the plasma concentration of the direct FXa inhibitor.

In other embodiments, the plasma concentration of an FXa variant sufficient to reverse the effect of a direct FXa inhibitor is calculated by multiplying the plasma concentration of the direct inhibitor by a conversion factor ranging from about $0.1\times10^{-4}$ to about $1000\times10^{-4}$, about $4\times10^{-4}$ to about $40\times10^{-4}$, about $20\times10^{-4}$ to about $200\times10^{-4}$, or other ranges. In yet other embodiments, the conversion factor can be about $0.1\times10^{-4}$, $0.5\times10^{-4}$, $1\times10^{-4}$, $2\times10^{-4}$, $3\times10^{-4}$, $4\times10^{-4}$, $5\times10^{-4}$, $6\times10^{-4}$, $7\times10^{-4}$, $8\times10^{-4}$, $9\times10^{-4}$, $10\times10^{-1}$, $11\times10^{-4}$, $12\times10^{-4}$, $13\times10^{-4}$, $14\times10^{-4}$, $15\times10^{-4}$, $16\times10^{-4}$, $17\times10^{-4}$, $18\times10^{-4}$, $19\times10^{-4}$, $20\times10^{-4}$, $21\times10^{-4}$, $22\times10^{-4}$, $23\times10^{-4}$, $24\times10^{-4}$, $25\times10^{-4}$, $26\times10^{-4}$, $27\times10^{-4}$, $28\times10^{-4}$, $29\times10^{-4}$, $30\times10^{-4}$, $31\times10^{-4}$, $32\times10^{-4}$, $33\times10^{-4}$, $34\times10^{-4}$, $35\times10^{-4}$, $36\times10^{-4}$, $37\times10^{-4}$, $38\times10^{-4}$, $39\times10^{-4}$, $40\times10^{-4}$, $45\times10^{-4}$, $50\times10^{-4}$, $55\times10^{-4}$, $60\times10^{-4}$, $65\times10^{-4}$, $70\times10^{-4}$, $75\times10^{-4}$, $80\times10^{-4}$, $85\times10^{-4}$, $90\times10^{-4}$, $95\times10^{-4}$, $100\times10^{-4}$, $110\times10^{-4}$, $120\times10^{-4}$, $130\times10^{-4}$, $140\times10^{-4}$, $150\times10^{-4}$, $160\times10^{-4}$, $170\times10^{-4}$, $180\times10^{-4}$, $190\times10^{-4}$, $200\times10^{-4}$, $250\times10^{-4}$, $300\times10^{-4}$, $350\times10^{-4}$, $400\times10^{-4}$, $450\times10^{-4}$, $500\times10^{-4}$, $550\times10^{-1}$, $600\times10^{-4}$, $650\times10^{-4}$, $700\times10^{-4}$, $750\times10^{-4}$, $800\times10^{-4}$, $850\times10^{-4}$, $900\times10^{-1}$, $950\times10^{-4}$, or $1000\times10^{-4}$, and ranges among these numbers. Plasma concentration of FXa direct inhibitor can be measured according to the knowledge of the skilled artisan, for example, by radio-immuno assay (RIA) or other method.

Achieving a target plasma concentration of FXa variant sufficient to reverse overdose of a direct FXa inhibitor is within the knowledge of those ordinarily skilled in the art. In a non-limiting example, estimates of relevant pharmacokinetic parameters, such as subject plasma volume or other parameters, can be made based on upon subject sex, height and weight, or other factors, and used to calculate how much FXa variant needs be administered to achieve the target concentration. After administering FXa variant, plasma concentrations can be monitored according to the knowledge of those ordinarily skilled in the art and this information used to maintain the concentration in any desired range.

The compositions and methods of the disclosure include a "therapeutically effective amount" or a "prophylactically effective amount" of an FXa variant. A "therapeutically effective amount" refers to an amount effective, at dosages and for periods of time necessary, to achieve the desired therapeutic result. A therapeutically effective amount of the FXa variant may vary according to factors such as the disease state, age, sex, and weight of the individual, and the ability of the FXa variant to elicit a descried response in the individual. A therapeutically effective amount is also one in which any toxic or detrimental effects of the FXa variant are outweighed by the therapeutically beneficial effects. A "prophylactically effective amount" refers to an amount effective, at dosages and for periods of time necessary, to achieve the desired prophylactic result. For example, a dose may be given prior to a planned surgery.

Dosage regimens can be adjusted to provide the optimum desired response (e.g., a therapeutic or prophylactic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the disclosure are dictated by and directly dependent on (a) the unique characteristics of the FXa variant and the particular therapeutic or prophylactic effect to be achieved, and (b) the limitations inherent in the art of compounding such an FXa variant for the treatment of individuals.

In certain embodiments, a therapeutically or prophylactically-effective amount of an FXa variant administered is about 0.0001 to 50 mg/kg, about 0.001 to 50 mg/kg, about 0.001 to 5 mg/kg, about 0.001 to 0.5 mg/kg, about 0.001 to 0.05 mg/kg, about 0.01 to 5 mg/kg or about 0.01 to 0.5 mg/kg.

In certain embodiments, a therapeutically or prophylactically-effective serum concentration of an FXa variant of the disclosure is about 0.0003 to 300 nM, about 0.003 to 300 nM, about. 0.03 to 300 nM, about 0.003 to 30 nM, about 0.03 to 30 nM or about 0.3 to 3 nM. The concentration of the FXa variant, for example in blood or plasma, may be measured by any method known in the art.

It is to be noted that dosage values may vary with FXa inhibitor concentration. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Another aspect of the present disclosure provides kits comprising an FXa variant or a composition comprising such an FXa variant. A kit may include, in addition to the FXa variant or composition, diagnostic or additional therapeutic agents. A kit can also include instructions for use in a therapeutic method, as well as packaging material such as, but not limited to, ice, dry ice, styrofoam, foam, plastic, cellophane, shrink wrap, bubble wrap, cardboard and starch peanuts. In one embodiment, the kit includes the FXa variant or a composition comprising it and one or more therapeutic agents that can be used in a method described herein.

The FXa variant may be administered, for example in a composition comprising it, once or multiple times to a subject until adequate hemostasis is restored or the direct FXa inhibitor or inhibitors are no longer effective. Where multiple administrations are used they may administered hourly, daily, or at any other appropriate interval, including for example multiple daily doses. Multiple doses may be administered on a schedule such as every 10 minutes, every 15 minutes, every 20 minutes, every 30 minutes, every hour, every two hours, every three hours, every four hours, three times daily, twice daily, once daily, once every two days, once every three days, and once weekly. The FXa variant may also be administered continuously, e.g. via a minipump. The FXa variant may be administered, for example, via a parenteral route (e.g., intravenously, subcutaneously, intraperitoneally, or intramuscularly). The FXa variant will generally be administered as part of a pharmaceutical composition as described below.

In another embodiment, the FXa variant may be co-administered with another procoagulant including another FXa variant, Factor IX, Factor XIa, Factor XIIa, Factor VIII, Factor Vila, FEIBA and prothrombin complex concentrate (PCC).

Co-administration of an FXa variant of the disclosure with an additional therapeutic agent (combination therapy) encompasses administering a pharmaceutical composition comprising the FXa variant and the additional therapeutic agent, as well as administering two or more separate pharmaceutical compositions, i.e., one comprising the FXa variant and the other(s) comprising the additional therapeutic agent(s). Co-administration or combination therapy further includes administering the FXa variant and additional therapeutic agent(s) simultaneously or sequentially, or both. For instance, the FXa variant may be administered once every three days, while the additional therapeutic agent is administered once daily at the same as the FXa variant, or at a different time. An FXa variant may be administered prior to or subsequent to treatment with the additional therapeutic agent. Similarly, administration of an FXa variant of the disclosure may be part of a treatment regimen that includes other treatment modalities including surgery. The combination therapy may be administered to prevent recurrence of the condition. The combination therapy may be administered from multiple times hourly to weekly. The administrations may be on a schedule such as every 10 minutes, every 15 minutes, every 20 minutes, every 30 minutes, every hour, every two hours, every three hours, every four hours, three times daily, twice daily, once daily, once every two days, once every three days, once weekly, or may be administered continuously, e.g. via a minipump. The combination therapy may be administered, for example, via a parenteral route (e.g., intravenously, subcutaneously, intraperitoneally, or intramuscularly).

In a further aspect, the disclosure provides a composition comprising an FXa variant for use in counteracting a direct FXa inhibitor in a subject. The composition may comprise a pharmaceutically acceptable carrier, vehicle or other ingredients that are physiologically compatible. Non-limiting examples of such carriers, vehicles and other ingredients include solvents (e.g., water, ethanol, saline, phosphate buffered saline), detergents, surfactants, dispersion media, coatings, antibacterial or antifungal agents, isotonifying agents, absorption delaying agents, sugars (e.g., sucrose, dextrose, lactose), polyalcohols (e.g., glycerol, mannitol, sorbitol), salts (e.g., sodium chloride, potassium chloride), wetting agents, emulsifying agents, preservatives, buffers, and agents capable of enhancing the stability or effectiveness of the FXa variant.

A composition for use according to the disclosure may be in any suitable form for administration to a subject, such as liquid solutions (e.g., injectable and infusible solutions). Compositions can be provided in a pre-mixed format ready for administration to a subject, for example, in a vial or pre-filled syringe. Such formats do not require reconstitution with diluent before administration. Alternatively, compositions can be provided in lyophilized form requiring reconstitution with diluent (e.g., sterile water or saline) before administration. If the latter, diluent can be provided with the lyophilisate in a separate container. According to the knowledge of those of ordinary skill in the art, compositions can be formulated for storage under refrigeration or at room temperature. The form of the composition depends, at least in part, on the intended mode of administration. In certain embodiments, the mode of administration is parenteral, including for example intravenous, subcutaneous, intraperitoneal, or intramuscular administration.

Therapeutic compositions typically must be sterile and stable under the conditions of manufacture and storage. The composition can be formulated as a solution, microemulsion, dispersion, in liposomes, or other ordered structure suitable to high drug concentration. Sterile injectable solutions can be prepared by incorporating the FXa variant in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

It is further contemplated by the present disclosure that any of the compositions herein may be administered to a subject being treated with a direct FXa inhibitor.

It is understood that the examples and embodiments described herein are for illustrative purposes only and that various modifications or changes in light thereof will be apparent to persons skilled in the art and are to be included within the and can be made without departing from the true scope of the invention.

EXAMPLES

Example 1—FXa$^{I16L}$ Sensitivity Toward Rivaroxaban

Figure 1B:
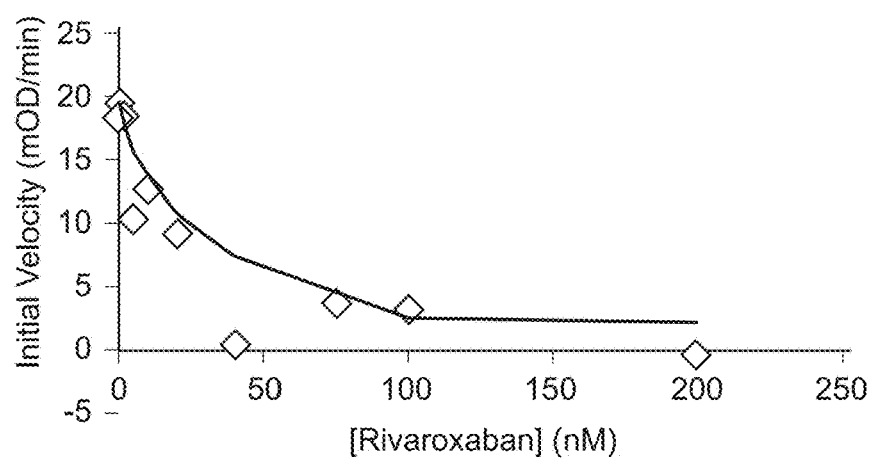
Figure 2A:
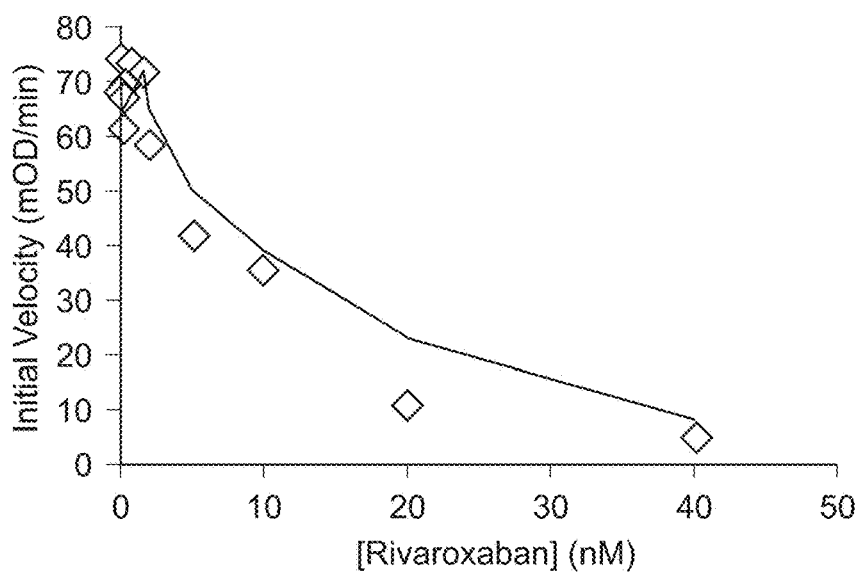
FIGS. 2A-B show rivaroxaban inhibition of wt-FXa or FXa$^{I16L}$ assembled in prothrombinase. The initial velocity of peptidyl substrate (SpecXa; 200 uM) hydrolysis by A) wt-FXa (2 nM) or B) FXa$^{I16L}$ (6 nM) in the presence of PCPS (20 uM) and FVa (40 nM) was determined at increasing concentrations of rivaroxaban.
Figure 2B:
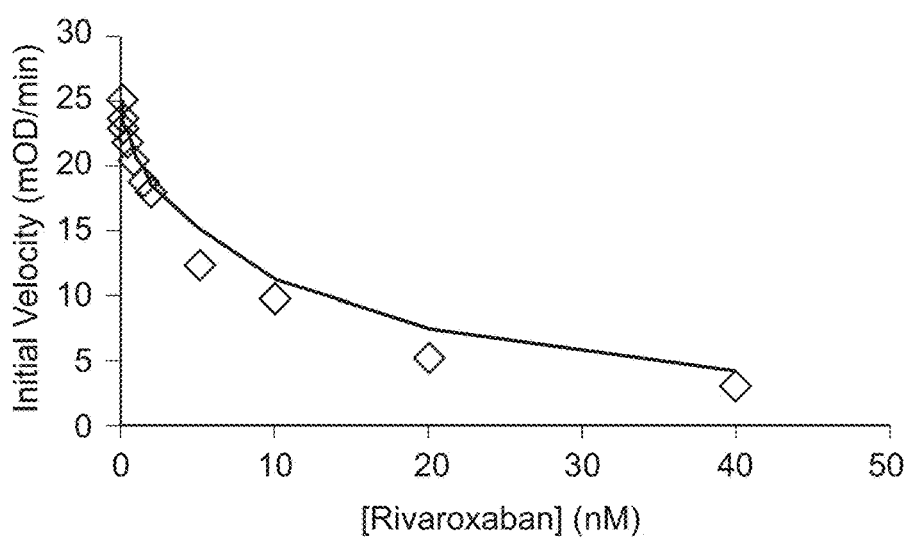
Figure 3:
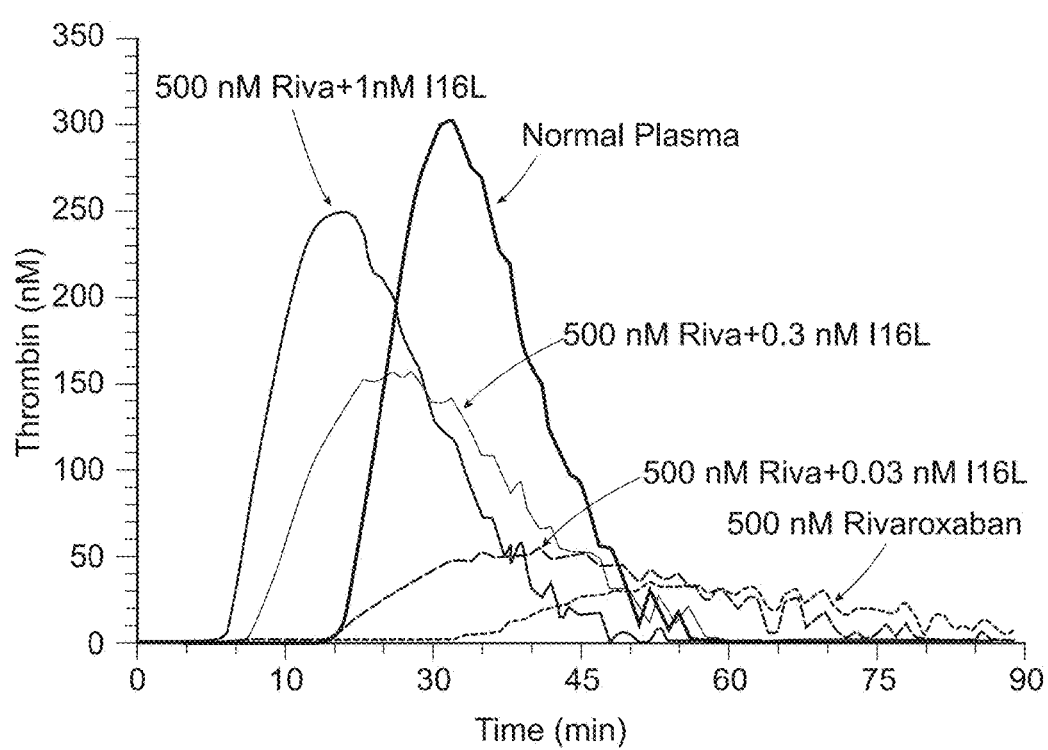
FIG. 3 shows the effect of different concentrations of FXa$^{I16L}$ on reversing the effects on thrombin generation of rivaroxaban.
Figure 4A:
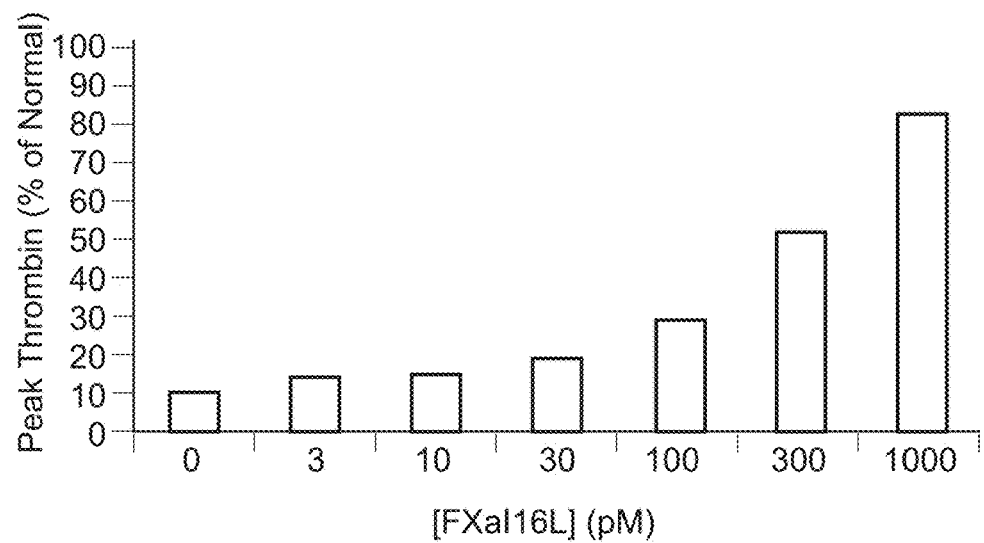
FIGS. 4A-D show the effect of FXa$^{I16L}$ on reversing the effects of rivaroxaban. Normal human plasma was incubated with 500 nM rivaroxaban and in the absence or presence of increasing concentrations of FXa$^{I16L}$. Following data analysis, peak thrombin (A and C) and total thrombin generated (ETP; B and D) were plotted.
Figure 4B:
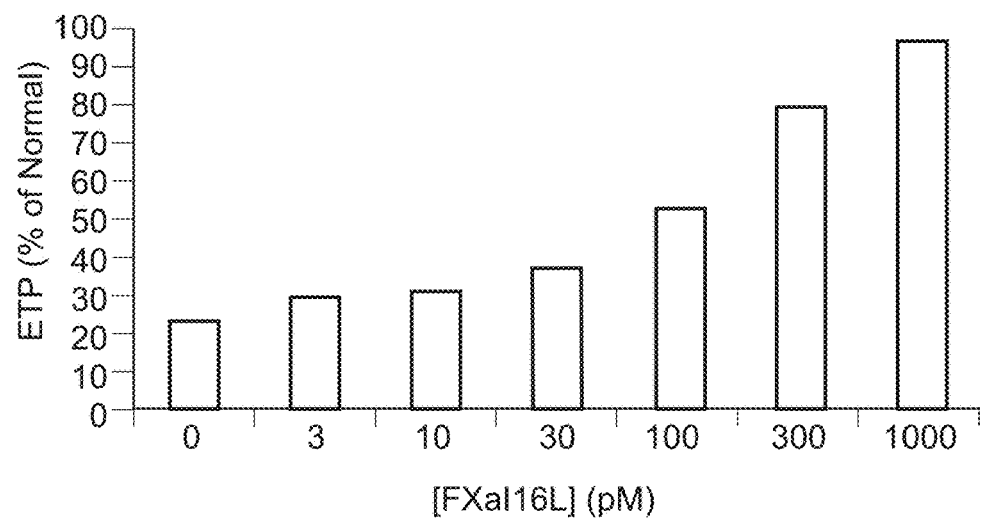
Figure 4C:
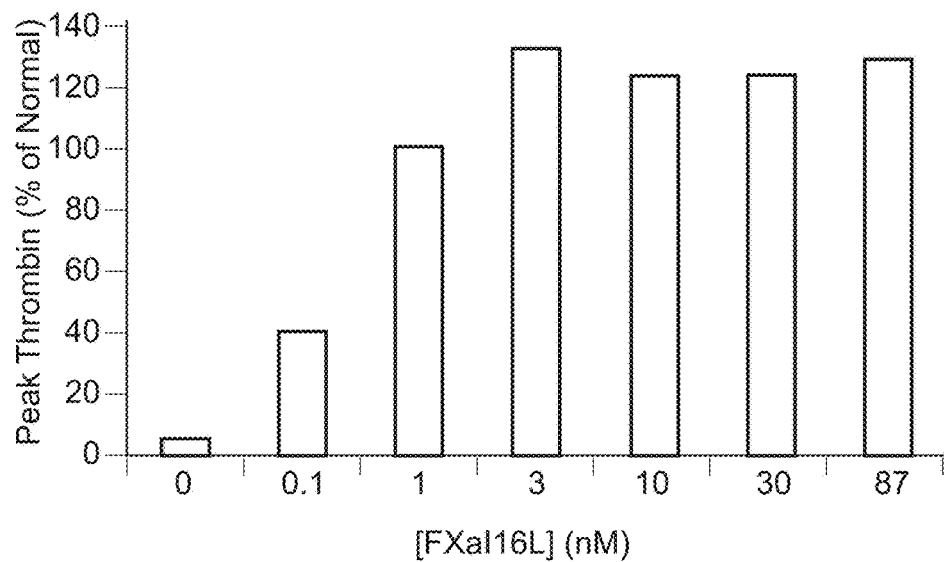
Figure 4D:
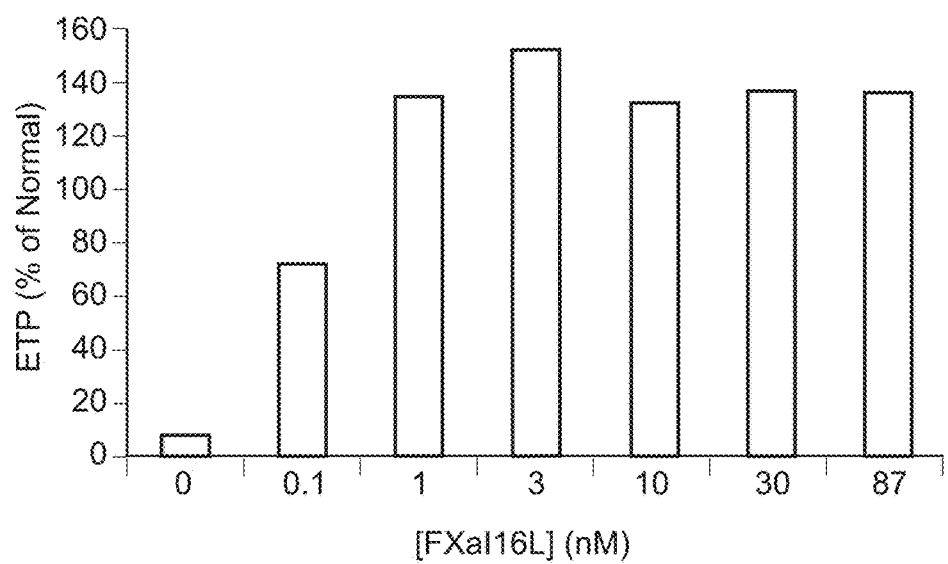
Figure 5A:
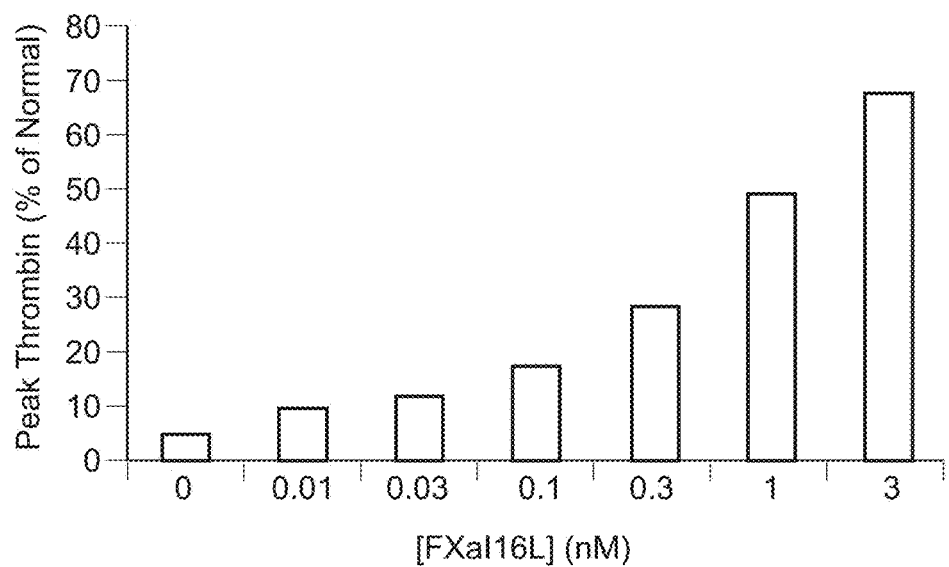
FIGS. 5A-B show FXa$^{I16L}$ reverses the effects of high dose rivaroxaban. Normal human plasma was incubated with 7.5 uM rivaroxaban and in the absence or presence of increasing concentrations of FXa$^{I16L}$. Following data analysis, peak thrombin (A) and total thrombin generated (ETP; B) were plotted.
Figure 5B:
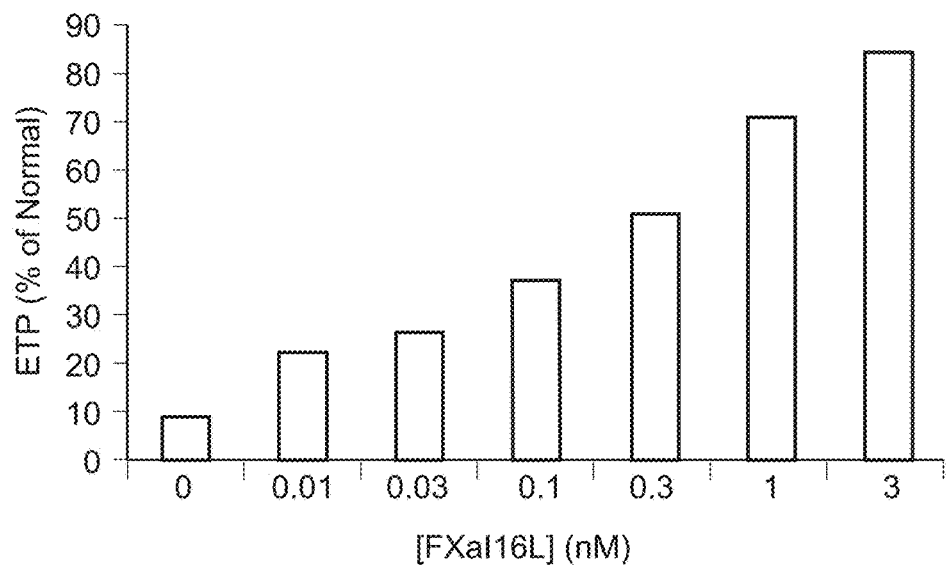
Figure 6A:
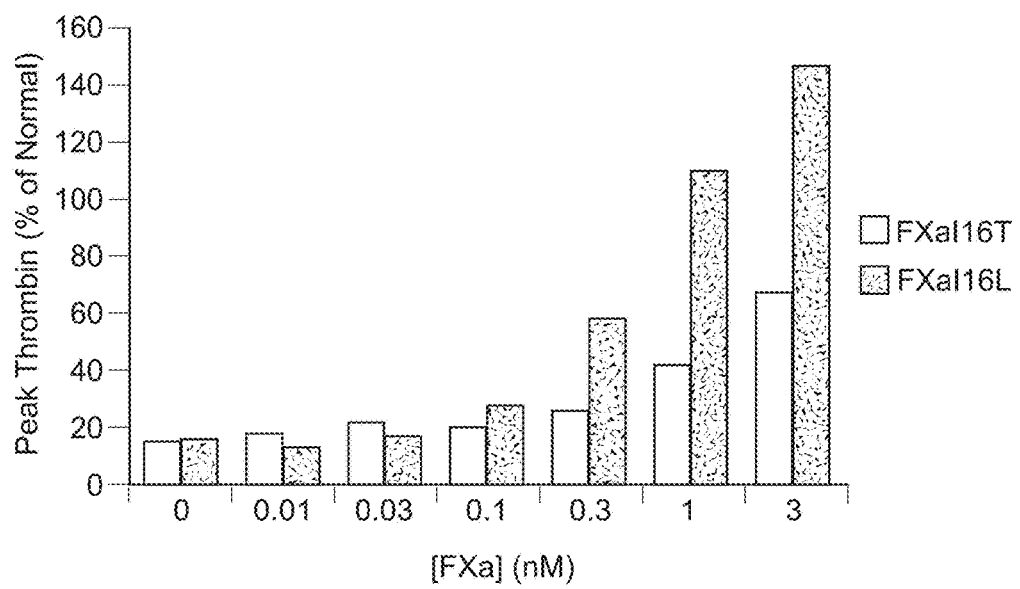
FIGS. 6A-B show FXa$^{I16L}$ or FXa$^{I16T}$ reverses the effects of 250 nM apixaban. Normal human plasma was incubated with 250 nM apixaban and in the absence or presence of increasing concentrations of FXa$^{I16L}$ or FXa$^{I16T}$. Following data analysis, peak thrombin (A) and total thrombin generated (ETP; B) were plotted.
Figure 6B:
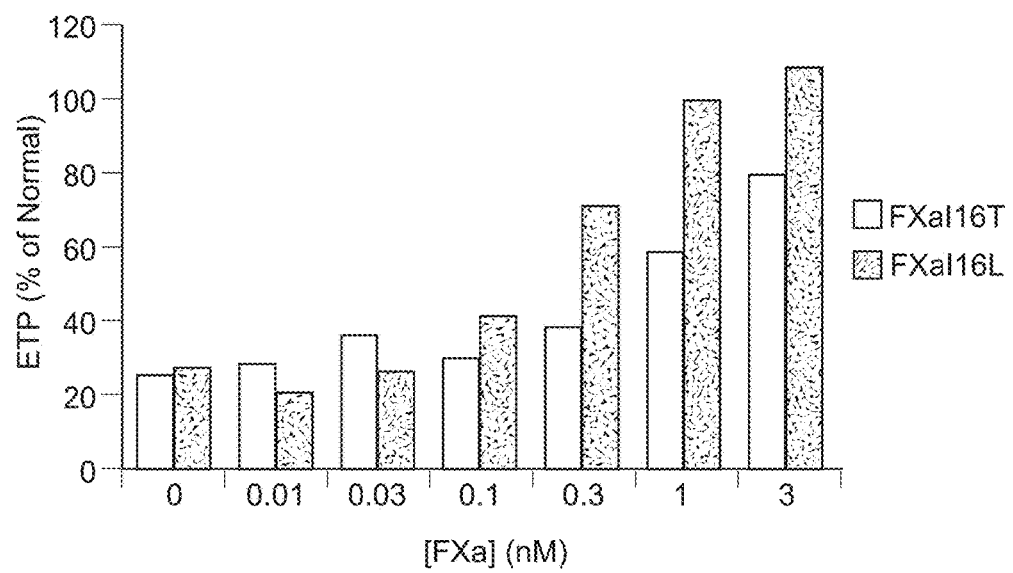
Figure 7A:
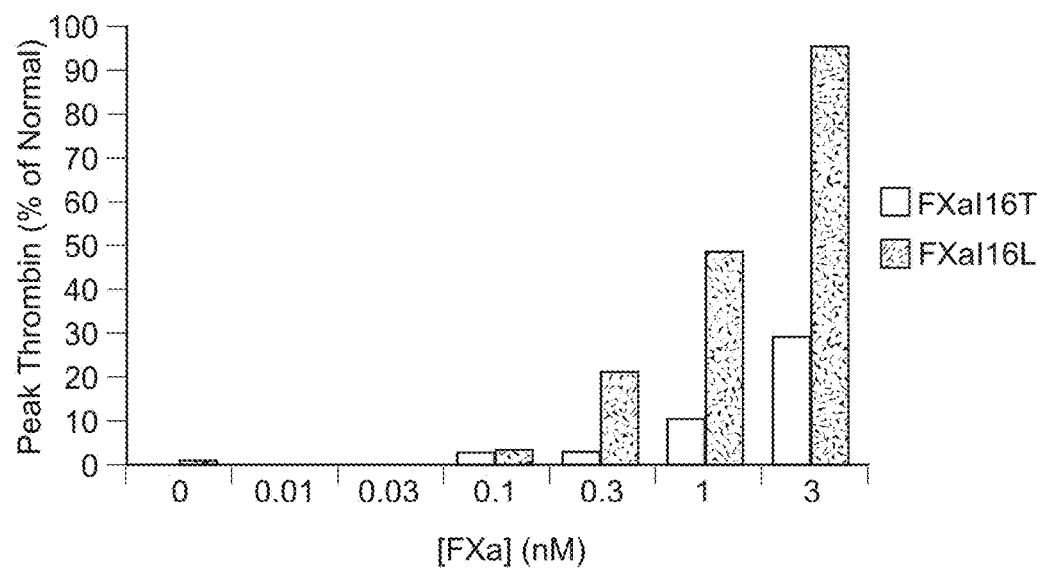
FIGS. 7A-B show FXa$^{I16L}$ or FXa$^{I16T}$ reverses the effects of high dose apixaban. Normal human plasma was incubated with 2.0 uM Apixaban and in the absence or presence of increasing concentrations of FXa$^{I16L}$ or FXa$^{I16T}$. Following data analysis, peak thrombin (A) and total thrombin generated (ETP; B) were plotted.
Figure 7B:
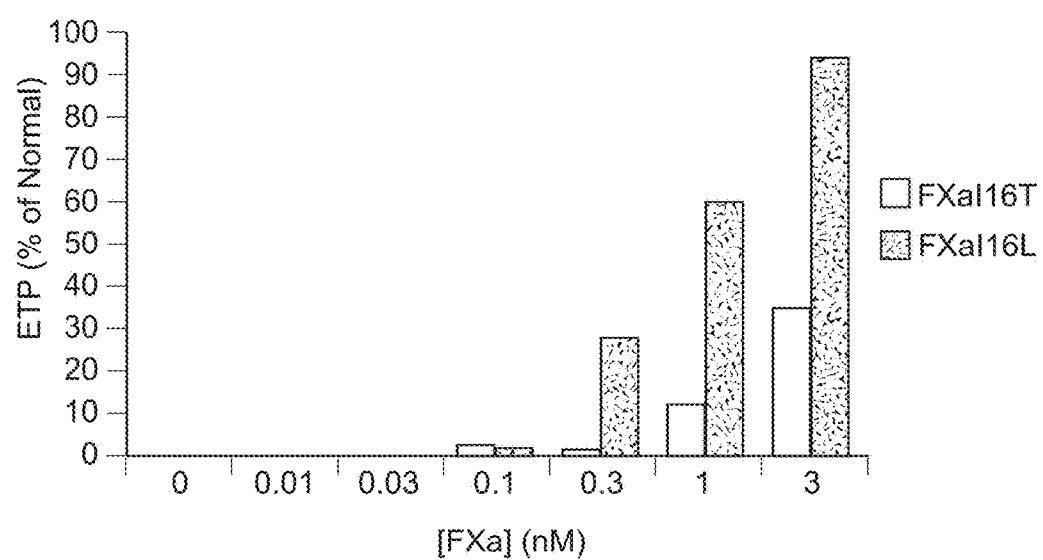
Figures 9A, 9B:
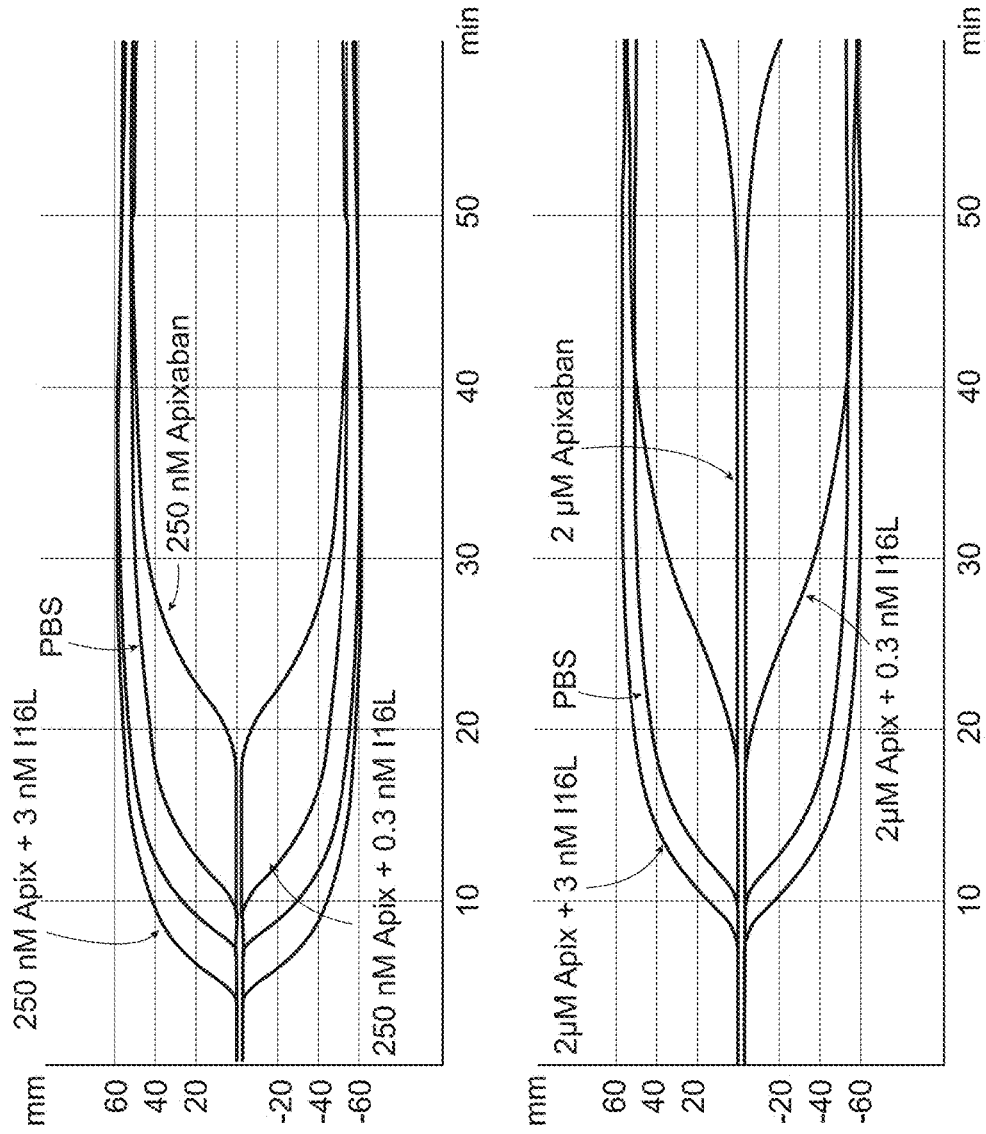
FIGS. 9A-B show FXa$^{I16L}$ corrects whole blood clotting in the presence of apixaban. Whole blood thromboelastography was used to assess the ability of FXa$^{I16L}$ to reverse the effects of apixaban at a typical (A) and a high (B) dose.

To test the sensitivity of FXa$^{I16L}$ toward rivaroxaban, inhibition assays were established. Rivaroxaban was an efficient inhibitor of wild-type FXa exhibiting an inhibition constant ($K_i$) of 0.582 nM (FIG. 1A). Due to the zymogen-like nature of FXa$^{I16L}$, rivaroxaban bound with a ~15-fold reduced affinity to this variant ($K_i$=9.3 nM) (FIG. 1B). In contrast, when the variant was assembled in the prothrombinase complex (i.e. upon addition of FVa and phospholipid vesicles), the $K_i$ for rivaroxaban was nearly restored to a value comparable to the wild-type enzyme (wt FXa, $K_i$=2.67 nM (FIG. 2A); $FXa^{I16L}$, $K_i$=3.4 nM (FIG. 2B).

Example 2—FXa Variants Counteract Rivaroxaban and Apixaban

The thrombin generation assay (TGA) was used to assess whether the zymogen-like FXa variants can reverse the effects of direct FXa inhibitors in a more physiologic environment. The TGA measures thrombin production in plasma over time following the initiation of coagulation and was performed as previously described (See Bunce et al., (2011) *Blood* 117, 290-298, incorporated by reference herein in their entirety). Thrombin generation in normal human plasma was measured for 90 min at 37° C. in the presence or absence of 500 nM rivaroxaban. To evaluate if $FXa^{I16L}$ can reverse the effect of rivaroxaban, increasing amounts of $FXa^{I16L}$ was added to plasma containing 500 nM rivaroxaban. Thrombin generation was initiated with 2.0 pM tissue factor/4 uM phospholipid as well as $CaCl_2$ and a thrombin fluorogenic substrate.

The data demonstrated that the thrombin generation profile of plasma in the presence of 500 nM rivaroxaban was substantially reduced compared to plasma in the absence of rivaroxaban. In contrast, increasing concentrations of $FXa^{I16L}$ from 0.03 to 1 nM restored thrombin generation (FIG. 3). These data show that unexpectedly low concentrations of $FXa^{I16L}$ in the nanomolar and subnanomolar range can reverse the effects of the inhibitor. Dose response analysis of $FXa^{I16L}$ in the presence of 500 nM rivaroxaban (a typical therapeutic plasma concentration) shows that the peak height of thrombin generation (FIGS. 4A and C) and total thrombin produced (ETP) (FIGS. 4 B and D) essentially reached a maximum and was completely restored to normal levels between 1-3 nM of $FXa^{I16L}$ under these conditions. Further experiments showed that even in the presence of high concentration of rivaroxaban (7.5 μM; supratherapeutic), $FXa^{I16L}$ was still quite effective at a relatively low dose (≤3.0 nM) in restoring peak thrombin (FIG. 5A) as well as total thrombin generated (FIG. 5B).

Similar experiments were also performed to evaluate whether FXa zymogen-like variants could reverse the effects of another direct FXa inhibitor, apixaban. In these experiments, the effectiveness of $FXa^{I16L}$ with another zymogen-like FXa variant, $FXa^{I16T}$, was also compared. $FXa^{I16T}$ is similar to $FXa^{I16L}$, however it has intrinsically less activity, has a longer plasma half-life, and has ~3-5-fold reduced activity compared to $FXa^{I16L}$ when assembled in the prothrombinase complex. Consistent with the rivaroxaban data, $FXa^{I16L}$ could restore peak thrombin (FIG. 6A) and total thrombin (FIG. 6B) generated in the presence of 250 nM apixaban (a typical therapeutic plasma concentration) in a dose-dependent manner, which appears to reach a maximum between 1-3 nM of $FXa^{I16L}$. $FXa^{I16L}$ was also effective at reversing the effects of apixaban; however, it appears that higher concentrations of this variant are needed to fully restore thrombin generation (FIG. 6). Both variants were still effective even in the presence of a higher concentration of apixaban (2 μM). However, under these conditions it appears that higher concentrations of both variants are needed to fully restore thrombin generation (FIGS. 7A and B).

Example 3—$FXa^{I16L}$ Counteracts Rivaroxaban and Apixaban in Whole Blood

Whole blood thromboelastometry was used to assess the ability of the $FXa^{I16L}$ variant to reverse the effects of the direct FXa inhibitors in whole blood. In this system, blood is drawn from healthy volunteers. The first 2 mL of blood were discarded and the subsequent 5 mL of blood was collected into a vacutainer (BID, Franklin Lakes, N.J.). Corn trypsin inhibitor and sodium citrate were in the collection tube, prior to collection of the blood sample, to achieve a final concentration of 0.105 M citrate and 25 μg/mL corn trypsin inhibitor (Haematologic Technologies, Burlington, Vt.) in the blood. Two sets of reactions were analyzed for each donor. The initial reaction initiated 5 minutes post blood collection. The second reaction initiated 1 hour post initiation of first reaction (1 hour 5 minutes after collection).

Blood was analyzed using Thromboelastometry ROTEM® delta (Tem International GmbH, Munich, Germany). For the reaction: (1) 6 μL of vehicle, protein, and/or inhibitor were added to the empty cup, (2) 20 μl of 0.2 M $CaCl_2$ (final concentration 11.6 mM), and (3) 20 μl of Innovin (final concentration in reaction 1:10,000; source of tissue factor) were added to the cup. Whole blood collected as described above was added to the reaction (300 up and recordings were allowed to proceed for approximately 30-60 minutes. The data collected was analyzed using the manufacture's software. (Rotem Gamma Software Version 1.1.1).

The ability of $FXa^{I16L}$ to accelerate whole blood clot formation in the presence of rivaroxaban or apixaban was examined using rotational thromboelastometry (ROTEM). Both direct FXa inhibitors alone and at two different concentrations have a substantial effect on whole blood clot formation: at low doses (therapeutic concentrations), whole blood clot formation is partially eliminated (FIG. 8A and FIG. 9A), while at high doses (supratherapeutic concentrations), whole blood clot formation is almost completely eliminated (FIG. 8B and FIG. 9B). The effects of either rivaroxaban or apixaban on whole blood clot formation could be reversed by $FXa^{I16L}$. In the presence of either 500 nM rivaroxaban or 250 nM apixaban, 0.3 nM $FXa^{I16L}$ could fully or nearly fully restore whole blood coagulation (FIG. 8A and FIG. 9A). When higher concentrations of the direct FXa inhibitors were used (~2 uM), 0.3 nM $FXa^{I16L}$ partially restored whole blood coagulation and 3 nM $FXa^{I16L}$ fully restored it (FIG. 8B and FIG. 9B). These data demonstrated that an FXa zymogen-like variant can effectively reverse the anticoagulant effect of rivaroxaban or apixaban in plasma-based and whole-blood coagulation assays at both therapeutic and supratherapeutic concentrations of the inhibitor.

Figure 12:
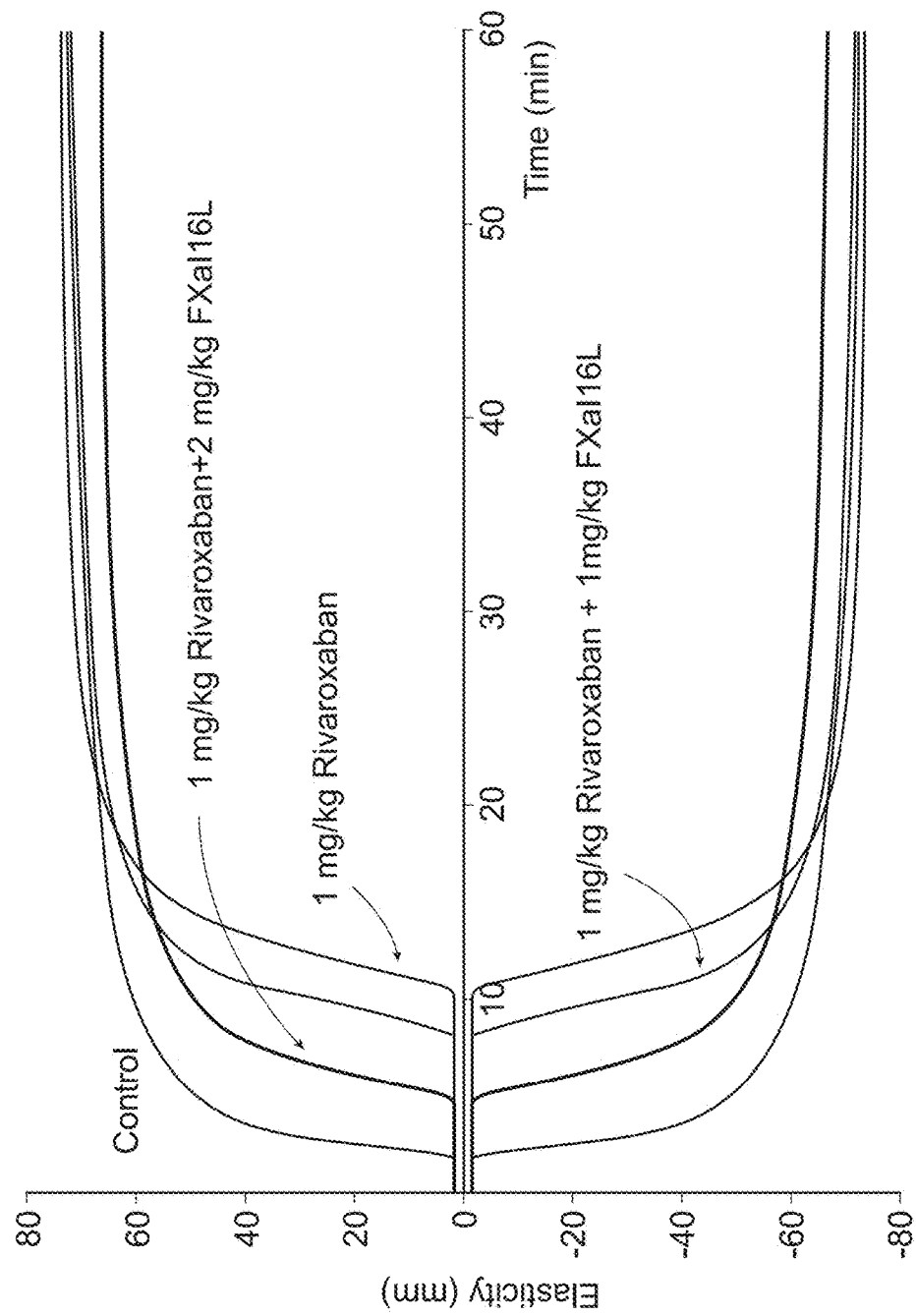
FIG. 12 demonstrates that rivaroxaban administered to mice delays clotting time of whole blood measured using ROTEM and that administration with FXa$^{I16L}$ dose-responsively counteracts the effect of rivaroxaban.

The results of these studies were confirmed and extended by testing if $FXa^{I16L}$ could counteract the anti-coagulant effect of rivaroxaban when both agents were administered in vivo. In these experiments, C57BL/6 mice were infused with rivaroxaban (1 mg/kg) or buffer via the tail vein. Mice were then prepared to expose the jugular vein and the vena cava. Approximately 10 min later $FXa^{I16L}$ (1 or 2 mg/kg) was infused by direct injection into the jugular vein. Five minutes post injection blood was collected via the vena cava into citrate and corn trypsin inhibitor. Collected blood was then analyzed by ROTEM using dilute tissue factor (Innovin, 1:42,000 dilution). Whole blood from mice administered buffer only clotted by about 2 min (FIG. 12). Administration of 1 mg/kg rivaroxaban substantially prolonged the clot time to about 10 min (FIG. 12). Further administration of $FXa^{I16L}$ shortened clotting time in the presence of rivaroxaban in a dose dependent manner (FIG. 12).

Example 4—$FXa^{I16L}$ Counteracts Rivaroxaban in a Thrombin Generation Assay

The effect of $FXa^{I16L}$ on reversing rivaroxaban in plasma was examined in a thrombin generation assay (TGA) using the calibrated automated thrombography (CAT) system (Thrombinoscope BV, Maastricht, The Netherlands). Normal human plasma was obtained from George King Biomedical (Overland Park, Kans.). In the reaction, 20 µL of PPP-Reagent LOW containing 4 µM phospholipids and 1 pM tissue factor was added to 70 µL of pooled citrated normal human plasma (treated with 250 nM rivaroxaban, within the therapeutic plasma concentration range) in an Immulon 2HB round bottom 0.96 well plate with reactions duplicated. Immediately preceding reaction initiation, 10 µL of vehicle or $FXa^{I16L}$ was added to plasma at final concentrations ranging from 0.03125 nM to 0.5 nM $FXa^{I16L}$, given a 120 µL total reaction volume. Reactions were initiated by addition of 20 µL FluCa buffer containing calcium chloride and fluorogenic substrate. Fluorescence of plasma reactions was read at 37° C. at 20 second intervals on a Fluoroskan Ascent fluorometer and compared to those of reference thrombin calibrator reactions to determine thrombin concentrations. The intensity of the fluorescence signal (FU) was continuously monitored at 37° C. using the CAT. Thrombin generation curves (nM thrombin vs. time) were analyzed to extract lag time, peak height, time to peak, and the area under the curve representing the endogenous thrombin potential (ETP) using the Thromboscope software (Thrombinoscope BV version).

Figure 10B:
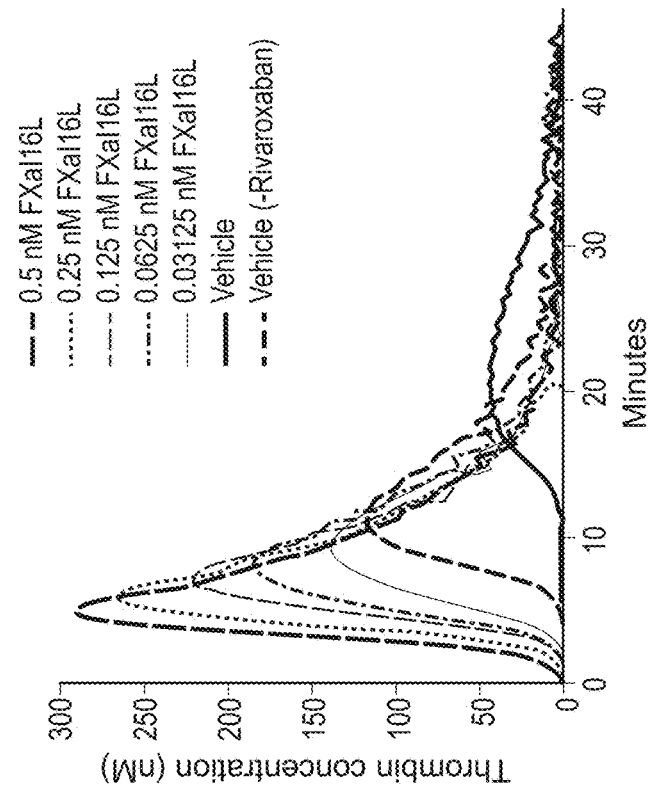
FIGS. 10A-B show that FXa$^{I16L}$ counteracts rivaroxaban in a thrombin generation assay.
Figure 10A:
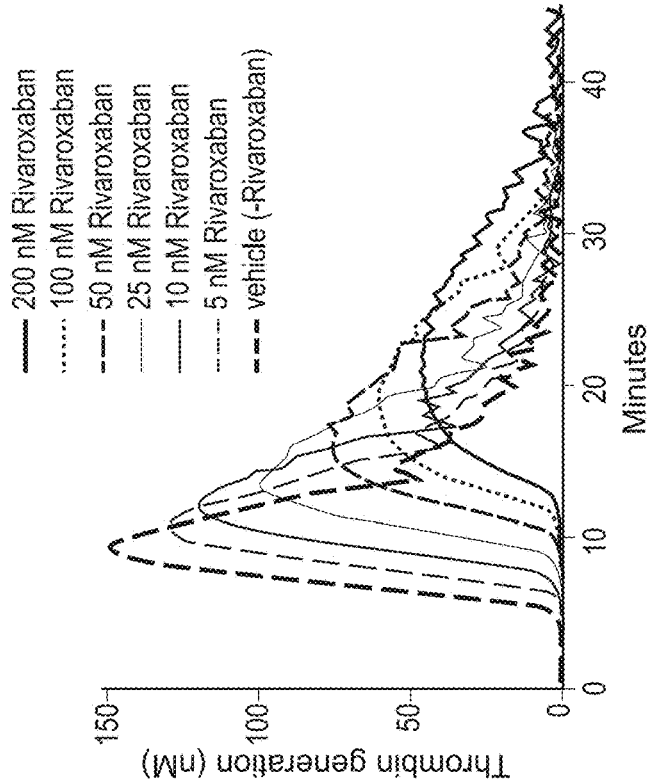

A dose dependent inhibition of thrombin generation in normal human plasma was observed with in vitro rivaroxaban treatment (5-200 nM) (FIG. 10A). Rivaroxaban resulted in an increase in the lag time coupled with a decrease in the peak thrombin and a decrease in the ETP. The addition of $FXa^{I16L}$ to rivaroxaban (250 nM) inhibited human plasma resulted in a dose dependent reversal of thrombin inhibition (FIG. 10B): peak thrombin generation was restored, the lag phase was shorter, and the ETP increased. At a low dose of 0.03125 nM $FXa^{I16L}$, thrombin generation was restored to levels comparable to vehicle treated normal human plasma.

Example 5—$FXa^{I16L}$ Counteracts Rivaroxaban in a Mouse Tail Clip Bleeding Model The ability of $FXa^{I16L}$ to overcome the effects of rivaroxaban in vivo was assessed in an acute bleeding model in normal mice. The results demonstrated that a zymogen-like FXa variant could reverse the anticoagulant effect of a direct FXa inhibitor.

Figure 11:
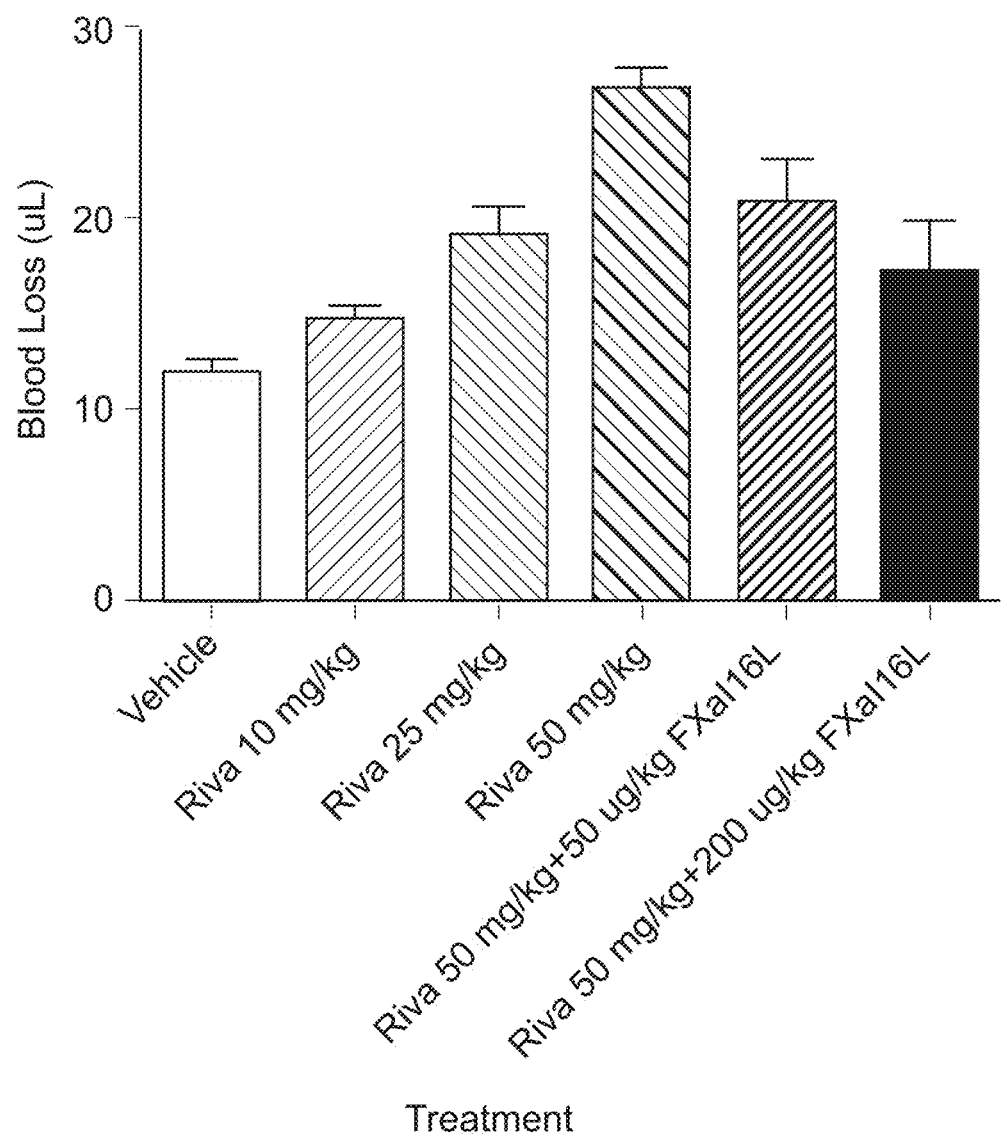
FIG. 11 shows that FXa$^{I16L}$ counteracts rivaroxaban in a mouse tail clip bleeding model.

To establish a dose of rivaroxaban that would prolong bleeding, male C57Bl/6 mice (The Jackson Laboratory, Bar Harbor, Me.) received a single intravenous injection of rivaroxaban at a dose of 10, 25 or 50 mg/kg. Thirty minutes later, mice were anesthetized with isoflurane and placed on a heated platform, and the body temperature of the mice was maintained at 37° C. prior to the tail cut. The tails were immersed in 50 mL pre-warmed phosphate buffered saline (PBS) at 37° C. for 2 minutes. A 3 mm tail cut was made and blood was collected into PBS for a 10 minute period. A quantitative assessment of the amount of bleeding was determined by hemoglobin content of the blood collected into PBS. Tubes were centrifuged to collect erythrocytes, resuspended in 5 mL lysis buffer (8.3 g/L $NH_4Cl$, 1.0 g/L $KHCO_3$, and 0.037 g/L EDTA), and the absorbance of the sample was measured at 575 nm. The absorbance values were converted to total blood loss (µL) using a standard curve. The administration of rivaroxaban resulted in a dose dependent increase in blood loss following a tail cut (FIG. 11).

In this model, a dose of 50 mg/kg rivaroxaban resulted in an increase in blood loss following the tail transfection. Mice were dosed with 50 mg/kg rivaroxaban and 30 minutes later 50 or 200 ug/kg of $FXa^{I16L}$ was dosed intravenously at 37° C. prior to the tail cut. Mice were then anesthetized with isoflurane and placed on a heated platform, and the body temperature of the mice was maintained at 37° C. prior to the tail cut. The tails were immersed in 50 mLs pre-warmed phosphate buffered saline (PBS) at 37° C. for 2 minutes. A 3 mm tail cut was made and blood was collected into PBS for a 10 minute period and the assessment of the amount of bleeding was determined by hemoglobin content as described. In this model, the administration of the hemostatic $FXa^{I16L}$ variant decreased the excessive bleeding loss induced with rivaroxaban (FIG. 11).

Example 6—$FXa^{I16L}$ Counteracts Rivaroxaban in a Mouse Bleeding Model Demonstrated Using Intravital Microscopy As visualized using intravital microscopy, rivaroxaban was demonstrated to inhibit thrombus formation in the microcirculation of the mouse cremaster muscle after laser-induced injury. Further administration of $FXa^{I16L}$ could counteract the anti-coagulant effect of rivaroxatran in this system.

Using standard techniques, the cremaster muscle of mice was exposed and visualized using intravital microscopy. A vascular injury in the muscle was then induced using a laser. After injury, clot formation was visualized using different fluorescently labeled antibodies that specifically recognize fibrin and platelets. Clotting is indicated by the presence of fluorescent signal from both types of antibodies.

Figure 13A:
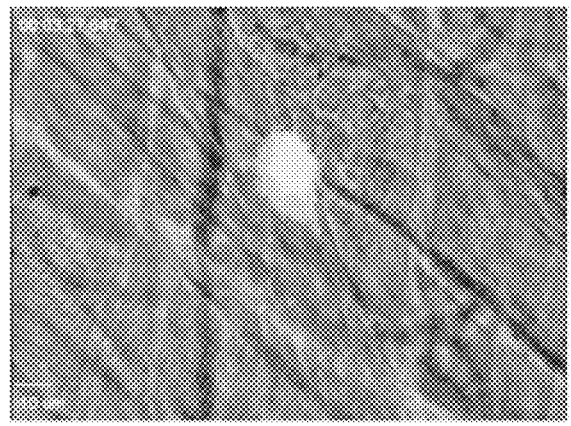
FIGS. 13A, 13B, and 13C show that rivaroxaban administered to a mouse prevents clot formation at a site of vascular injury in the cremaster muscle caused by laser and that administration with FXa$^{I16L}$ counteracts the effect of rivaroxaban. Clot formation was visualized using intravital microscopy and fluorescently labeled antibodies against fibrin and platelets.
Figure 13B:
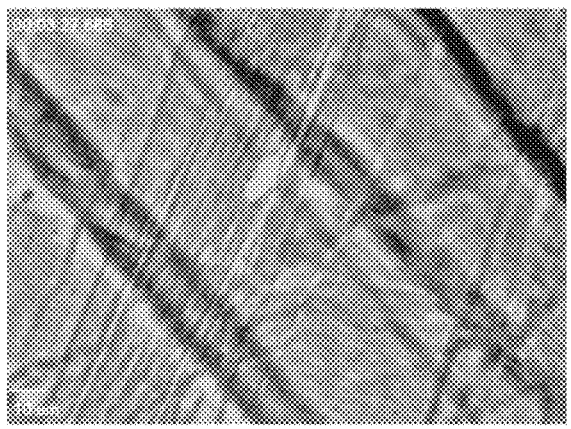
Figure 13C:
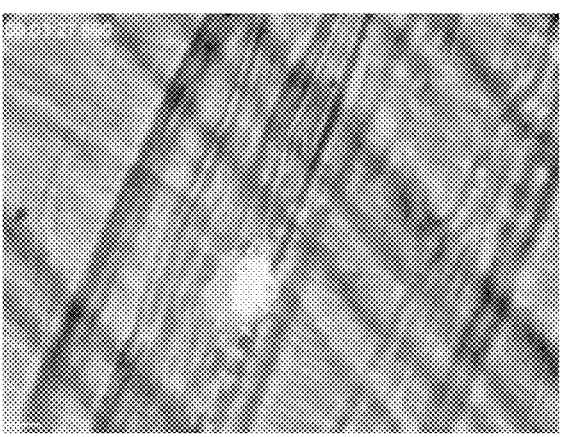

After laser injury, an untreated mouse rapidly formed a clot at the site of injury that was stable for several minutes (FIG. 13A). In the video frame, the clot is visible as the coincidence of fluorescent signal associated with antibodies against fibrin and platelets (light gray center region overlapping darker gray region). Administration of 1 mg/kg rivaroxaban to a mouse, however, delayed the accumulation of platelets at the injury site and eliminated any signs of fibrin (FIG. 13B). In the video frame, only a reduced extent of platelets can be seen as indicated by the dark gray region, which reflects presence of fluorescent signal associated with anti-platelet antibodies. By contrast, when a mouse was administered 1 mg/kg rivaroxaban followed by 0.5 mg/kg FXa$^{I16L}$, a clot rapidly formed at the injury site (FIG. 13C). In the video frame, the clot is indicated by the characteristic pattern of fluorescent signal associated with antibodies against platelets and fibrin.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well known and commonly used in the art.

The methods and techniques of the present disclosure are generally performed according to conventional methods well known in the art and as described in various general and more specific references that are cited and discussed throughout the present specification unless otherwise indicated. See, e.g., Sambrook J. & Russell D. *Molecular Cloning: A Laboratory Manual*, 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology*, Wiley, John & Sons, Inc. (2002); Harlow and Lane *Using Antibodies: A Laboratory Manual*, Cold Spring Harbor Laboratory Press, Cold Spring Harbor, N.Y. (1998); and Coligan et al., *Short Protocols in Protein Science*, Wiley, John & Sons, Inc. (2003), incorporated herein by reference. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well known and commonly used in the art.

All publications, patents, patent applications or other documents cited herein are hereby incorporated by reference in their entirety for all purposes to the same extent as if each individual publication, patent, patent application, or other document was individually indicated to be incorporated by reference for all purposes.

Throughout this specification and claims, the word "comprise," or variations such as "comprises" or "comprising," will be understood to imply the inclusion of a stated integer or group of integers but not the exclusion of any other integer or group of integers.

What is claimed is:

1. A method for reversing the anticoagulant effect of a direct Factor Xa inhibitor in a subject, comprising administering to said subject a Factor Xa variant that contains at least one modification selected from the group consisting of:
   a) the amino acid at the position corresponding to 235 in SEQ ID NO:1 is substituted with Thr, Leu, Phe, Asp or Gly; and
   b) the amino acid at the position corresponding to 236 in SEQ ID NO:1 is substituted with Leu, Ala, or Gly,
   wherein said subject has acute major bleeding and acquired coagulopathy due to FXa inhibition therapy using a direct FXa inhibitor,
   wherein reversal of the anticoagulant effect of the direct Factor Xa inhibitor effects the urgent reversal of the acquired coagulopathy due to FXa inhibition therapy in said subject with acute major bleeding; and
   wherein said Factor Xa variant is effective to reverse the anticoagulant effect of the direct Factor Xa inhibitor at a plasma concentration at least 250-fold lower than the plasma concentration of the direct Factor Xa inhibitor.

2. The method of claim 1, wherein reversal of the anticoagulant effect of the direct Factor Xa inhibitor results in a reduction in bleeding of at least about 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, or 95%400%.

3. The method of claim 1 wherein reversal of the anticoagulant effect of the direct Factor Xa inhibitor results in the amount of thrombin being produced to increase by at least about 10%, 20%, 30%, 40%, 50%, 60%, 70%, 80%, 90%, 95%, 100%, 1.5-fold, 2-fold, 3-fold, 4-fold, 5-fold, 6-fold, 7-fold, 10-fold, 15-fold, 20-fold, 25-fold, 30-fold, or 50-fold.

4. The method of claim 1 wherein reversal of the anticoagulant effect of the direct Factor Xa inhibitor results in reduction in clotting time of at least about 5%-10%, 10%-15%, 15%-20%, 20%-25%, 25%-30%, 30%-35%, 35%-40%, 40%-45%, 45%-50%, 50%-55%, 55%-60%, 60%-65%, 65%-70%, 70%-75%, 75%-80%, 80%-85%, 85%-90%, 90%-95%, or 95%-100%.

5. The method of claim 4, wherein the reduction in clotting time is measured using prothrombin time (PT).

6. The method of claim 5, wherein said PT in said subject is about 25 seconds, 24 seconds, 23 seconds, 22 seconds, 21 seconds, 20 seconds, 19 seconds, 18 seconds, 17 seconds, 16 seconds, 15 seconds, 14 seconds, 13 seconds, 12 seconds, 11 seconds, or 10 seconds.

7. The method of claim 5, wherein the International Normalized Ratio (INR) in said subject is about 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, or 0.7.

8. The method of claim 5, wherein PT is determined 15 mins, 20 mins, 30 mins, 40 mins, 45 mins, 50 mins, 60 mins, 75 min, or 90 min after administration of the FXa variant.

9. The method of claim 1, wherein the Factor Xa variant is administered before a planned surgery, after an injury or after a direct Factor Xa inhibitor overdose.

10. The method of claim 1, wherein Factor Xa variant is administered more than one time.

11. The method of claim 1, wherein at least one additional procoagulant is administered.

12. The method, composition or use of claim 11, wherein the procoagulant is selected from the group consisting of: a different Factor Xa variant, Factor IX, Factor XIa, Factor XIIa, Factor VIII, Factor VIIa, FEIBA and prothrombin complex concentrate (PCC).

13. The method of claim 1, wherein the plasma concentration of the direct FXa inhibitor is a supratherapeutic amount.

14. The method of claim 1, wherein the direct FXa inhibitor is rivaroxaban, apixaban, betrixaban, darexaban, edoxaban, or otamixaban.

15. The method of claim 1, wherein the plasma concentration of the direct FXa inhibitor is at least about 50 nM, 100 nM, 150 nM, 200 nM, 250 nM, 300 nM, 350 nM, 400 nM, 500 nM, 600 nM, 700 nM, or 800 nM.

16. The method of claim 1, wherein the Factor Xa variant is administered in a dose range of 0.0001 to 50 mg/kg, 0.001 to 50 mg/kg, 0.001 to 5 mg/kg, 0.001 to 0.5 mg/kg, 0.001 to 0.05 mg/kg, 0.01 to 5 mg/kg, or 0.01 to 0.5 mg/kg.

17. The method of claim 1, wherein the Factor Xa variant is administered to achieve a plasma concentration in a range of 0.0003 to 300 nM, 0.003 to 300 nM, 0.03 to 300 nM, 0.003 to 30 nM, 0.03 to 30 nM, or 0.3 to 3 nM.

18. A method for reversing the anticoagulant effect of a direct Factor Xa inhibitor in a subject, comprising administering to said subject a Factor Xa variant comprising Leu at the position corresponding to 235 in SEQ ID NO:1,
wherein said subject has acute major bleeding and acquired coagulopathy due to FXa inhibition therapy using a direct FXa inhibitor,
wherein reversal of the anticoagulant effect of the direct Factor Xa inhibitor effects the urgent reversal of the acquired coagulopathy due to FXa inhibition therapy in said subject with acute major bleeding; and
wherein said Factor Xa variant is effective to reverse the anticoagulant effect of the direct Factor Xa inhibitor at a plasma concentration at least 250-fold lower than the plasma concentration of the direct Factor Xa inhibitor.

19. The method of claim 18, wherein said Factor Xa variant is effective to reverse the anticoagulant effect of the direct Factor Xa inhibitor at a plasma concentration at least 500-fold lower than the plasma concentration of the direct Factor Xa inhibitor.

20. The method of claim 18, wherein said Factor Xa variant is effective to reverse the anticoagulant effect of the direct Factor Xa inhibitor at a plasma concentration at least 1000-fold lower than the plasma concentration of the direct Factor Xa inhibitor.

* * * * *